(12) United States Patent
Ahmad et al.

(10) Patent No.: US 7,744,929 B2
(45) Date of Patent: Jun. 29, 2010

(54) BOTANICAL DRUG COMPOSITIONS FOR TREATMENTS OF LIVER AND IMMUNOLOGICAL DISORDERS

(75) Inventors: Hassan Ahmad, Paterson, NJ (US); Ismail Elchagea, Nutley, NJ (US); Ezz Hamza, Bardonia, NY (US)

(73) Assignee: Ambotan Pharma, LLC, Paterson, NJ (US)

( * ) Notice: Subject to any disclaimer, the term of this patent is extended or adjusted under 35 U.S.C. 154(b) by 0 days.

(21) Appl. No.: 10/662,777

(22) Filed: Sep. 15, 2003

(65) Prior Publication Data

US 2005/0058735 A1    Mar. 17, 2005

(51) Int. Cl.
*A61K 36/00* (2006.01)

(52) U.S. Cl. .................................... 424/725

(58) Field of Classification Search ................ 424/725
See application file for complete search history.

(56) References Cited

U.S. PATENT DOCUMENTS

| 5,648,089 | A | * | 7/1997 | Shawkat ................ 424/434 |
| 5,653,981 | A | * | 8/1997 | Medenica ............... 424/776 |
| 6,841,174 | B2 | * | 1/2005 | Shalaby et al. .......... 424/725 |
| 7,592,327 | B2 | * | 9/2009 | Nassief .................. 514/54 |
| 2002/0132019 | A1 | * | 9/2002 | Kandil ................... 424/764 |
| 2002/0160065 | A1 | * | 10/2002 | Shalaby et al. .......... 424/764 |
| 2004/0067263 | A1 | * | 4/2004 | Liu et al. ................ 424/725 |

OTHER PUBLICATIONS

Khan, M.A.U. et al. "The In Vivo Antifungal Activity of the Aqueous Extract from *Nigella sativa* Seeds," Phytotherapy Research, vol. 17, No. 2, pp. 183-186 (Feb. 2003).*
Türkdoğan et al.; "The Role of Antioxidant Vitamins (C and E), Selenium and *Nigella sativa* in the Prevention of Liver Fibrosis and Cirrhosis in Rabbits: New Hopes," Dtsch. Tierarztl. Wschr. 108, 71-73, Feb. 2001. (3 pages total).*
Internet website www.botanical.com/botanical/mgmh/l/livame26.html (3 pages total) "Botanical—A Modern Herbal: *Anemone hepatica*" (2002).*

* cited by examiner

*Primary Examiner*—Christopher R. Tate
(74) *Attorney, Agent, or Firm*—Thomas J. Germinario

(57) ABSTRACT

The present invention relates to compositions comprising the botanicals from the Family Ranunculaceae, Subclass: Dicotyledonae; Crassinucelli, Superorder: Ranunculales. Examples of these botanicals include but are not limited to; *Actaea, Anemone, Ranunculus*, and *Nigella*, or extracts thereof, which are useful in treating liver diseases, particularly those with viral etiology. More specifically, the compositions of the present invention are derived from various botanicals or medicinal plants. The compositions of the invention have demonstrated outstanding efficacy for treatment of patients with hepatic disorders. Compositions of the present invention have also exhibited immunomodulatory activities. The preferred compositions contain the botanical ingredients in concentrations of not less than 20% w/v. The treatment can be therapeutic or prophylactic and may be administered orally, parenterally, as suppository or via nasal mucosa. The treatment may be delivered in a single dose, multi-doses or via a slow release mechanism.

11 Claims, 11 Drawing Sheets

BOTANICAL DRUG COMPOSITIONS FOR TREATMENTS OF LIVER AND IMMUNOLOGICAL DISORDERS

FIELD OF THE INVENTION

This invention relates to novel medicinal compositions derived from botanical medications, medicinal plants, and their extracts thereof, and to their use for the treatment of liver and immunological disorders. The compositions of the present invention are derived from the family Ranunculaceae and are obtained through specific techniques rendering pharmacologically effective compositions of not less than 20% w/v concentration. The invention further provides for pharmaceutical compositions for oral, parenteral, topical, and nasal delivery as well as by suppository. Solid dosage-forms, liquids, suspensions, intramuscular, subcutaneous, intravenous, and transdermal delivery systems are contemplated by the present invention, as are nasal sprays.

BACKGROUND OF THE INVENTION

Modern medical science is constantly searching for new and more powerful agents to prevent, treat, or retard infections and cure the diseases they cause. The cost of treating theses infections is astronomical, and can be in the range of billions of dollars every year. Vast sums of money are spent each year by pharmaceutical companies to identify, characterize, and produce new drugs. Reliable prophylactic treatments for disease prevention are also of major interest. Yet, despite the costs and the efforts to identify treatments for viral infections such as hepatitis, effective therapies remain elusive.

Hepatitis is a disease of the human liver. It is manifested with inflammation of the liver and is usually caused by viral infections and sometimes results from exposure to toxic agents. The hepatitis C virus (HCV) is spread through blood. It can infect people for long periods of time without causing obvious symptoms, but prolonged inflammation eventually damages the liver. Healthy liver cells are replaced by scar tissue that can keep the organ from functioning properly. Hepatitis may progress from fibrosis to liver cirrhosis, liver cancer, and eventually death. Death from the disease could triple over the next twenty years, as old infections reach clinical stages. Twenty percent of the carriers suffer acute viral hepatitis, 60-70% chronic hepatitis, and 30% cirrhosis, end-stage liver disease, and liver cancer (Chen, D. S. et al. (1996) Medical Assoc., 95(1):6-12).

Four millions Americans (about 1.8% of the USA population) have antibodies for HCV. Hepatitis C causes an estimated 8,000-12,000 deaths per year in the USA. The total deaths expected to be more than triple by the year 2010, which are about 38,000 per year, unless more effective treatments are found. World Health Organization (WHO) estimates that about 170 million people, 3% of the world's population are at risk of developing liver cirrhosis, and/or liver cancer. The prevalence of HCV-infection in some countries in Africa, the Eastern Mediterranean, South-East Asia and Western Pacific is high compared to some countries in North America and Europe. The following Table 1 shows Hepatitis C estimated prevalence and number infected by WHO Region.

TABLE 1

Hepatitis C Prevalence and Number Infected by WHO Region

| WHO Region | Total Population (Millions) | Hepatitis C Prevalence (Rate %) | Infected Population (Millions) | Number of countries by WHO Region where data are not available |
|---|---|---|---|---|
| Africa | 602 | 5.3 | 31.9 | 12 |
| Americas | 785 | 1.7 | 13.1 | 7 |
| Eastern Mediterranean | 466 | 4.6 | 21.3 | 7 |
| Europe | 858 | 1.03 | 8.9 | 19 |
| South-East Asia | 1500 | 2.15 | 32.3 | 3 |
| Western Pacific | 1600 | 3.9 | 62.2 | 11 |
| Total | 5811 | 3.1 | 169.7 | 57 |

Currently there is no effective cure or vaccine for HCV. Medications are available to slow down or stop the damage to the liver caused by HCV. The therapy for chronic hepatitis C has evolved steadily since alpha interferon was first approved for use in this disease more than 10 years ago. At the present time, the optimal regimen appears to be a 24- or 48-week course of the combination of pegylated alpha interferon and ribavirin. Treatment of HCV with interferon alone results in only about a 50% success rate. However, half of those responding relapse after cessation of interferon treatment. Therefore, only about 25% of the patients have a sustained response. It also gives rise to several side effects that cannot be tolerated by about 10% of the patients. Such side effects include severe flu symptoms. Many patients will consider stopping treatment because of these very troublesome symptoms, which include lethargy, hair loss, neuropsychiatric side effects, gastrointestinal symptoms, skin reactions, hormonal and metabolic symptoms, and undesirable tastes in the mouth. Some rare side effects can cause death from acute myocardial infarctions, strokes, suicides and sepsis.

Two forms of peginterferon have been developed and studied in large clinical trials: peginterferon alfa-2a (Pegasys: Hoffman La Roche: Nutley, N.J.) and peginterferon alfa-2b (Pegintron: Schering-Plough Corporation, Kenilworth, N.J.). These two products are roughly equivalent in efficacy and safety, but have different dosing regimens. Peginterferon alfa-2a is given subcutaneously in a fixed dose of 180 micrograms (mcg) per week. Peginterferon alfa-2b is given subcutaneously weekly in a weight-based dose of 1.5 mcg per kilogram per week (thus in the range of 75 to 150 mcg per week).

Ribavirin is an oral antiviral agent that has activity against a broad range of viruses. By itself, ribavirin has little effect on HCV, but adding it to interferon increases the sustained response rate by two- to three fold. For these reasons, combination therapy is now recommended for hepatitis C, and interferon monotherapy is applied only when there are specific reasons not to use ribavirin. Ribavirin is given twice a day in 200-mg capsules for a total daily dose based upon body weight. The standard dose of ribavirin is 1,000 mg for patients who weigh less than 75 kilograms (165 pounds) and 1,200 mg for those who weigh more than 75 kilograms. In certain situations, an 800-mg dose (400 mg twice daily) is recommended. Interferon acts against the virus via the immune system and does not reverse any physiological abnormalities or damage caused by the infection itself, e.g. hepatic cirrhosis.

In the United States three different regimens have been approved as therapy for hepatitis C: monotherapy with alpha interferon, combination therapy with alpha interferon and ribavirin, and pegylated interferon therapy. Interferon therapy costs $480/month ($5,760/year), Rebetron Combination therapy costs $1,560/month ($18,720/year), PEG-intron therapy costs $960-$1,114/month ($11,544-$13,368/year).

Prior to the availability of liver transplantation, the management of end-stage liver disease was limited to efforts to correct and control the complications associated with cirrhosis, and to comfort measures when all avenues had been exhausted. In the last decade, however, orthotopic liver transplantation has become an accepted treatment for patients with end-stage liver disease. However, management of the patient following transplantation has led to a wide variety of new challenges. The serious complications of end-stage liver disease and the decreased quality of life is the primary cause for the indication of liver transplantation. Clearly, patients with variceal bleeding, refractory ascites, hepatic encephalopathy, osteopenia, and malnutrition have a decreased quality of life due to the significant morbidity and potential mortality of each of these complications. In most cases, the indication for transplantation is easily recognized by the referring physician. The timing of referral for liver transplantation plays a crucial role in the management and survival of patients with end-stage liver disease. As the waiting lists and waiting times lengthen, the condition of the patient at the time of referral is of critical importance. Unfortunately, the number of patients dying on transplantation waiting lists is increasing (Todo, S. et al. (1991) Hepatology 13:619-626).

Table 2 summarizes transplantation data for the entire United States, including the number of candidates currently on the waiting list, by organ type. Included in this table are the totals for the number of transplants performed and donors recovered during the time periods specified.

TABLE 2

Transplantation Data for the United States

Waiting list candidates as of Mar. 25, 2003

| | |
|---|---:|
| All | 80,639 |
| Kidney | 53,843 |
| Pancreas | 1,404 |
| Kidney/Pancreas | 2,403 |
| Liver | 16,957 |
| Intestine | 187 |
| Heart | 3,760 |
| Lung | 3,817 |
| Heart/Lung | 198 |

*All candidates will be less than the sum due to candidates waiting for multiple organs Transplants performed January-December 2002

| | |
|---|---:|
| Total | 25,765 |
| Deceased Donor | 19,160 |
| Living Donor | 6,605 |

Donors recovered January-December 2002

| | |
|---|---:|
| Total | 12,794 |
| Deceased Donor | 6,184 |
| Living Donor | 6,610 |

*Based on OPTN data as of Mar. 21, 2003

Viral hepatitis has become a difficult problem for transplant centers before and after transplantation. Hepatitis B recurs in the transplanted liver in 80%-90% of patients. Hepatitis C is found in 20%-30% of patients at most transplant centers, and infection of the allograft occurs in 40%-45% of patients at one year post-transplant. These figures have led to the exclusion of hepatitis B patients from transplantation at many centers and careful consideration of patients with hepatitis C.

Post liver transplantation has led to a wide variety of new challenges; Infection of the allograft with hepatitis C leading to recurrent of disease, Cholestatic liver disease, Hepatocellular carcinoma, Biliary complications, Hyperlipidemia and Obesity, Graft-versus-Host Disease, and Chimerism (*Liver Transplantation: The Hepatology Perspective* by Jeffrey S. Crippin).

If the hepatitis virus could be eradicated prior to the time of transplantation, post-transplantation morbidity would likely be decreased. Unfortunately, therapeutic options are limited to interferon, an agent used with limited success in the non-transplant setting.

Immunological disorders have long been known as one of the serious health problems in the world. While the percentage of affected population and severity of the diseases are rising, current methods of treatment still primarily depend on empirical and serendipitous findings rather than from a scientific approach. At present, most patients are treated with drugs that aim at controlling symptoms resulted from the release of mediators by the effector cells. Although some drugs appear to be effective over a short-term and with few occurrence of adverse effects, long-term effects for preventing disease progression and permanent destruction are still largely unknown. For example, long-term oral therapy, such as steroid therapy, for treating asthma, is known to be associated with multiple debilitating effects such as growth delay, osteoporosis, and adrenal suppression. (Janeway, C. A. et al. (1994) Current Biology Ltd.).

Most of the marketed immunomodulators show non-reproducible and ambiguous results. Isolated or recombinant peptides and protein molecules (interferons, interleukins, antibodies, and vaccines) are very expensive and demonstrate many side effects and uncertain activities.

Immunomodulators offer a powerful tool for the control of host immunity by amplification or by suppression of the body's immune system. Stimulation of immunity is important in the host's defense against infectious diseases and cancer. Immunomodulators may activate macrophages that subsequently release mediators, including growth factors and cytokines. Immunomodulators may be used in the treatment of individuals with compromised immune system in order to enhance their immune response (Paul, W. E. (1989) Raven Press Ltd.). On the other hand, certain diseases may benefit from treatment with agents that down-regulate the immune system. For example, in patients suffering from autoimmune disorders, or in patients undergoing a transplant, it would be beneficial to treat with an agent that suppresses the immune response.

There is a great need to develop new immunomodulators which have significant immunomodulating activities, while at the same time exhibiting less toxicity, and which are readily accessible as compared to the marketed agents.

SUMMARY OF THE INVENTION

The Family Ranunculaceae, commonly referred to as the Buttercup family, has been around for hundreds of years. Although there are no accounts of fossil records or of the botanical or shrub, there are accounts of early settlers and ancient rituals that involve the Ranunculaceae plant. The Ranunculaceae family is very common around the world in a variety of climates such as North America, India, Africa, and South America etc. People have been experimenting for decades on how to benefit from the Ranunculaceae. From accumulative technology, the people of the world have used these botanical plants for a variety of uses, such as treatments of fevers, boils, and rheumatism. It is an object of the present invention to provide a novel and effective composition derived from members of the family Ranunculaceae for treating liver and immunological disorders.

Accordingly, many members of the family Ranunculaceae can be used for treatment of a variety of conditions, including skin diseases, hemorrhoids, cancer, endothelial cell progression, decrease in the production of the angiogenic protein-fibroblastic growth factor made by tumor cells and inhibition of the growth factor made for endothelial cells. The present invention provides for novel compositions and methods of use for botanicals that are members of the family Ranunculaceae and extracts derived from these plants. In particular, the present invention provides for compositions comprising botanicals from the family: Ranunculaceae, subclass: Dicotyledonae; Crassinucelli, superorder: Ranunculales. Compositions comprising these botanicals include but are not limited to; *Actaea, Anemone, Ranunculus*, and *Nigella*, or extracts thereof, which are useful in treating liver diseases, particularly those with viral etiology. The compositions of the invention are obtained through specific techniques and have demonstrated outstanding efficacy for treatment of patients with hepatic disorders. Compositions of the present invention have also exhibited immunomodulatory activities in experimental rats. It is envisioned that the compositions of the present invention may prove to be beneficial in clinical situations whereby there is a need for immunomodulatory activity. Furthermore, the compositions of the present invention may prove to be beneficial in situations where there is a need for upregulation of certain cells of the immune system, such as for treatment of patients whose immune system is compromised (e.g. cancer patients or AIDS patients). On the other hand, certain of the compositions of the present invention may prove to be beneficial in situations where there is a need for down-regulation of certain cells in the immune system. For example, in autoimmune disorders or in transplant patients, it is beneficial to down-regulate certain cells of the immune system. Thus, immunomodulatory compositions may encompass both immune enhancers as well as immune depressants. That is, an immunomodulatory composition, as used herein, helps to restore the immune cell populations to normal levels. The preferred compositions contain the botanical ingredients in concentrations of not less than 20% w/v. The treatment can be effective when used either as a therapeutic or when given prophylactically and may be administered orally, parenterally, topically, as suppository or via nasal mucosa. The treatment may be delivered in a single dose, multi-doses or via a slow release mechanism.

Accordingly, in a first aspect, the invention provides for a composition comprising a botanical plant of the family Ranunculaceae, or extracts thereof. In a preferred embodiment the invention provides for a composition, which comprises at least one of the botanical plants *Actaea, Anemone, Nigella*, and *Ranunculus*, or extracts thereof, and a pharmaceutically acceptable carrier. In another preferred embodiment the invention provides for a composition, which comprises at least one of the botanical plants *Actaea Rubra, Anemone hepatica, Anemone Nemorosa, Nigella sativa*, and *Ranunculus Arvensis*, or extracts thereof and a pharmaceutically acceptable carrier. These compositions are useful for treating hepatitis and immunological disorders, although other therapeutic or prophylactic uses are also contemplated.

The extracts may be present in a relative ratio to each other of:

about 1% by weight to about 95% by weight of *Actaea rubra*, about 1% by weight to about 95% by weight of *Anemone hepatica*, about 1% by weight to about 95% by weight of *Anemone nemorosa*, about 1% by weight to about 95% by weight of *Nigella sativa*, about 1% by weight to about 95% by weight of *Ranunculus arvensis*, Preferably, the extracts may be present in a ratio of:

about 2% by weight to about 90% by weight of *Actaea rubra*, about 2% by weight to about 90% by weight of *Anemone hepatica*, about 2% by weight to about 90% by weight of *Anemone nemorosa*, about 2% by weight to about 90% by weight of *Nigella sativa*, about 2% by weight to about 90% by weight of *Ranunculus arvensis*, Still more preferably, the extracts may be present in a ratio of:

about 5% by weight to about 15% by weight of *Actaea rubra*, about 40% by weight to about 87% by weight of *Anemone hepatica*, about 2% by weight to about 7% by weight of *Anemone nemorosa*, about 4% by weight to about 12% by weight of *Nigella sativa*, about 7% by weight to about 23% by weight of *Ranunculus arvensis*, In a second aspect, the invention provides for concentrating the botanical plant(s) extract(s) to produce sterile preparations of not less than 20% w/v. Accordingly, a composition is prepared wherein the extract from at least one of the plants from the family Ranunculaceae is concentrated and sterilized rendering a sterile preparation with a concentration of not less than 20% weight per volume. In another embodiment, the extracts from two or more plants from the family Ranunculaceae are prepared and combined to produce a synergistic effect in treating hepatic disorders or as an immunomodulatory composition.

In a third aspect, the invention provides for methods of treating hepatic disorders. Preferably, the hepatic disorder treated is caused by a viral infection such as hepatitis C virus. Particularly, the invention provides for a method of treating hepatic disorders caused by hepatitis C virus infection using the compositions of the present invention. In one embodiment, treatment consists of administration of a composition to patients with clinical stages 0/6, 1/6, 2/6, and 3/6, with corresponding hepatic activity index ranging from 1/18 to 9/18, requiring such treatment. In another embodiment, the invention provides for a method of treating hepatic disorders caused by hepatitis C virus infection, comprising administration of a composition to patients with clinically advanced stages, i.e. 4/6, 5/6, and 6/6, with corresponding hepatic activity index ranging from 7/18 to 13/18, requiring such treatment. In a more preferred embodiment, the hepatic disorders being treated result from chronic hepatitis. In a yet further embodiment, the hepatic disorders result from genotypes I, II, III, IV. In a preferred embodiment, the extract from at least one of the plants from the family Ranunculaceae is prepared, concentrated and sterilized and concentrated to not less than 20% w/v and used to treat hepatic or immunologic disorders. This treatment may be used therapeutically or prophylactically.

In a fourth aspect, the invention provides for methods of treating immunological disorders. In a preferred embodiment, the extract from at least one of the plants from the family Ranunculaceae is prepared, concentrated and sterilized and concentrated to not less than 20% w/v and used to treat hepatic or immunologic disorders. In another embodiment, the extracts from two or more plants from the family Ranunculaceae are prepared and combined to produce a synergistic effect in treating hepatic or immunological disorders. These treatments may be used therapeutically or prophylactically.

More preferably the immunological disorders treated are caused by a viral infection that compromises the immune system. Non-limiting infections for which the botanical compositions may be effective are those common in patients having human immunodeficiency viruses or infections common in patients whose immune system is compromised following chemotherapy or irradiation therapy for various cancers. These may include infections with herpesviruses, such as cytomegalovirus, or bacterial infections acquired through long hospital stays, including nosocomial infections. Examples may include, but shall not be limited to, infections with gram positive and gram negative bacteria. In particular, infections with methicillin resistant *Staphylococcus aureus* infections, or infections attributed to *Pseudomonas* species or tuberculosis are also envisioned as a target for treatment with the compositions of the present invention.

In a fifth aspect, the invention provides for a method of increasing the number and/or the activity of specific immune cells, in particular, white blood cells including lymphocytes. In a preferred embodiment, the invention provides for increasing the number and/or the activity of natural killer cell populations, comprising administration of a composition of the present invention to a patient requiring such treatment. A yet further preferred embodiment provides for increasing the natural killer cell population in patients having hepatic disorders, including but not limited to hepatitis. Another embodiment provides for increasing the natural killer cell population in patients having AIDS, or in patients who are immunocompromised, such as cancer patients undergoing chemotherapy or radiation therapy, wherein the stem cell or hematopoietic blood cell precursors for immune cells, including T and B lymphocytes, as well as natural killer cells, is destroyed by chemotherapy or radiation treatments. A yet further embodiment provides for normalization of T and/or B lymphocyte numbers and/or activity in patients in need of such normalization by treatment with the compositions of the present invention. A yet further embodiment provides for increasing or normalizing platelet counts in patients in need of such therapy by treatment with the compositions of the present invention.

In a sixth aspect, the invention provides for pharmaceutical compositions, comprising at least one plant or plant extract from the family Ranunculaceae that may be administered orally, parenterally, as a transdermal system, as a suppository or via the nose. In another embodiment, the extracts from two or more plants from the family Ranunculaceae are prepared and combined to produce a synergistic effect in treating hepatic or immunological disorders that may be administered orally, parenterally, as a transdermal system, as a suppository or via the nose. These treatments may be used therapeutically or prophylactically. The parenteral route could be topical, intramuscular, intravenous, or subcutaneous. The treatment may be delivered in a single bolus dose, multi-doses, or via a slow release mechanism. In another embodiment, the composition may be in the form of a tablet or capsule or it may be in the form of a suspension or liquid. In another embodiment, it may be formulated as an injectable. In another embodiment, the invention provides for a method of treating hepatic disorders, without adversely affecting the hemoglobin blood level.

In one embodiment, it is envisioned that treatment with the compositions of the present invention may be as stand alone therapy, or the compositions may be used as adjunct therapy with other anti-viral or anti-bacterial agents. Furthermore, the compositions of the present invention may be used with other agents commonly used to treat hepatic disorders, including but not limited to hepatitis, such as the interferons. They may also be used with anti-inflammatory agents or with standard pain medications, or with other treatment regimens useful in treating the disorder under consideration. In yet another embodiment, the compositions of the present invention may also be used with other synthetic chemical or peptidic immunomodulators, cytokines, growth factors or colony stimulating factors that may act to restore immune function, peripheral blood cell counts or bone marrow cellularity. Examples may include GM-CSF, G-CSF, M-CSF, IL-3, IL-1 and IL-6.

In yet another embodiment, the compositions of the present invention may be used in combination with specific inhibitors of HCV-derived enzymes such as protease, helicase, and polymerase inhibitors. Drugs that inhibit other steps in HCV replication may also be helpful in treating this disease, by blocking production of HCV antigens from RNA (internal ribosome entry site (IRES) inhibitors), preventing the normal processing of HCV proteins (inhibitors of glycosylation), or blocking entry of HCV into cells (by blocking its receptor). In addition, nonspecific cytoprotective agents might be helpful for hepatitis C by blocking the cell injury caused by the virus infection. Furthermore, molecular approaches to treating hepatitis C are envisioned for use in combination with the compositions of the present invention. These consist of using ribozymes, which are enzymes that break down specific viral RNA molecules, and antisense oligonucleotides, which are small complementary segments of DNA that bind to viral RNA and inhibit viral replication.

In a seventh aspect, the invention provides for decreasing the viral load in liver-cancer patients by administration of the compositions of the present invention to a patient in need of such therapy. In one embodiment, the invention provides for decreasing the hepatitis C (HCV) viral load in liver cancer patients or patients inflicted by HIV-1 or HIV-2, or other viral infections to which AIDS patients may be susceptible, by administration of the compositions of the present invention. These include, but are not limited to, cytomegalovirus and other members of the herpesvirus family. The invention further provides for decreasing viral load in patients having both HCV and HIV-1 or 2.

In an eighth aspect, the invention provides for screening for novel compositions and/or plant extracts useful for treating hepatic disorders or treating immune deficiencies, comprising (a) exposing (treating) blood cells with and without treatment with test extracts; and (b) determining the effect of the test extract on blood cell populations, wherein test compounds capable of increasing immune cell integrity or preserving immune cell numbers are identified as immune enhancing agents. A preferred embodiment includes an in vitro screening method for the identification of novel compositions and/or plant extracts useful for treating hepatic disorders or treating immune deficiencies, comprising, incubation of blood cells obtained from a mammal with either a vehicle control, or with at least one of the extracts from the plants of the present invention as a positive control, or with a test extract, and monitoring the effect of the extracts on blood cell number and/or proliferation, or activity/function or on expression of cell surface markers. A further embodiment includes a screening method for identifying extracts capable of protecting immune cells from damage, comprising (a) treating immune cells with cytotoxic compounds in vitro or in vivo with and without treatment with a test extract; and (b) determining the effect of the test extract on the immune cell population, wherein a test extract capable of increasing cell survival is identified as an immunoprotective agent. A yet further embodiment provides for an in vivo method of screening for novel compositions and/or plant extracts useful for treating hepatic disorders or treating immune deficiencies comprising, injecting mammals with LPS, dividing the mammals into various treatment groups, treating one group with a vehicle control, the second group is treated with at least one extract from the plants of the present invention as a positive control, and a test extract, and obtaining blood cells from the mammals and monitoring the blood cells for cell surface markers or proliferative capacity or immune cell function and/or activity.

Other advantages of the present invention will become apparent from the ensuing detailed description taken in conjunction with the following illustrative drawings.

DETAILED DESCRIPTION OF THE INVENTION

Figure 1:
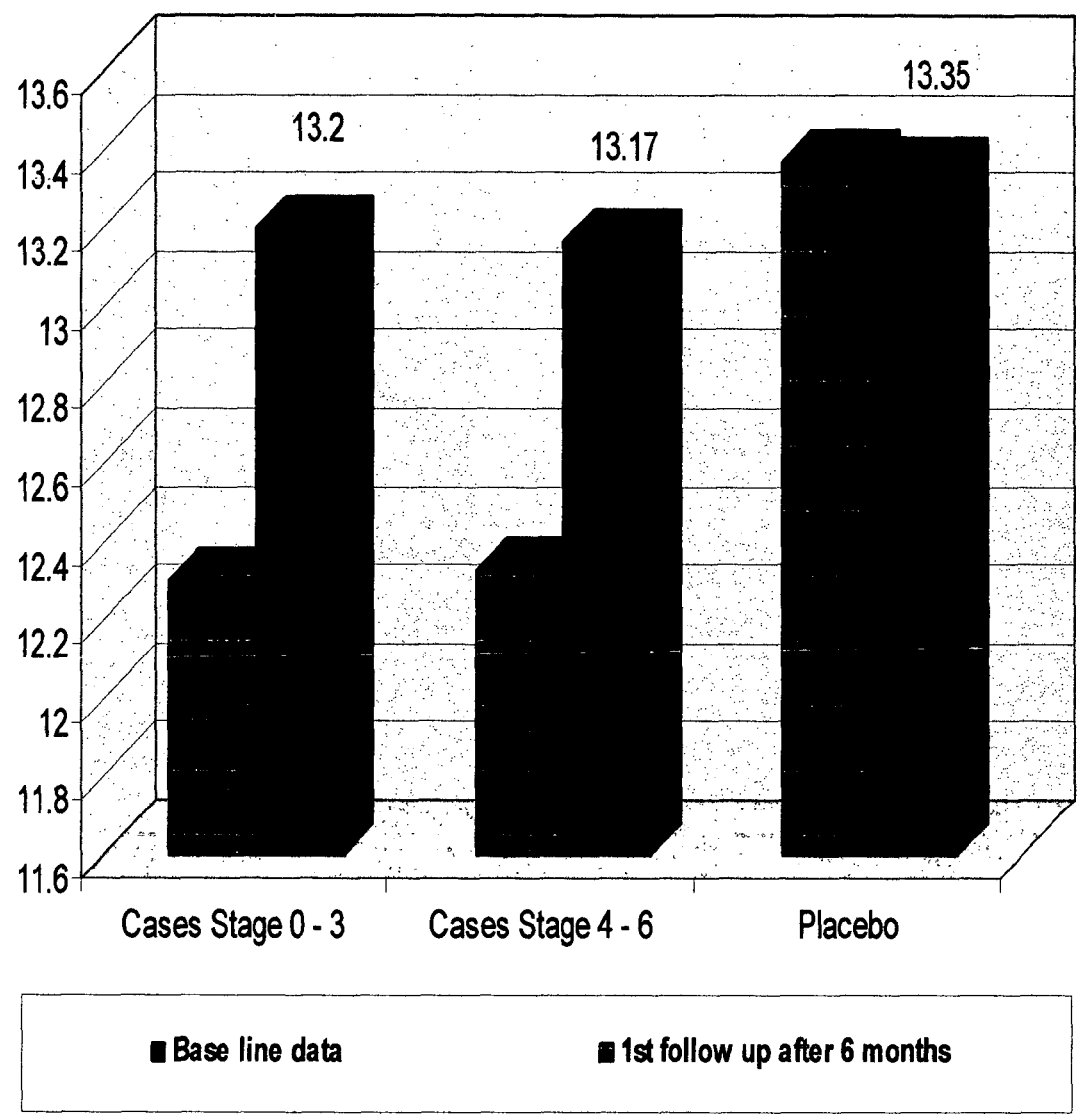
FIG. 1. Comparison of viral load of the two case groups with pathological stages of 0/6-3/6 and 4/6-6/6 and the placebo group after six months.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Definitions

The terms used herein have the meanings recognized and known to those of skill in the art, however, for convenience and completeness, particular terms and their meanings are set forth below.

"Treatment" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Agent" refers to all materials that may be used to prepare pharmaceutical and diagnostic compositions, or that may be chemical compounds, nucleic acids, polypeptides, fragments, isoforms, variants, or other materials that may be used independently for such purposes, all in accordance with the present invention.

A "therapeutically effective amount" is an amount sufficient to decrease or prevent the symptoms associated with the hepatic conditions or immunologic deficiencies contemplated for therapy with the compositions of the present invention.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of treatments necessary to achieve the desired effect in terms of decreasing the viral load associated with viral hepatitis or the symptoms associated with the disease, or in the treatment of immunodeficiencies, one would see a restoration to normalcy of certain lymphocyte populations, such as T or B cells or natural killer cells.

"Combination therapy" refers to the use of the agents of the present invention with other active agents or treatment modalities, in the manner of the present invention for treatment of hepatic disorders or immunological deficiencies. These other agents or treatments may include drugs such as other anti-viral drugs, corticosteroids, non-steroidal anti-inflammatory compounds, other agents useful in treating or alleviating pain, growth factors, cytokines, or colony stimulating factors. The combined use of the agents of the present invention with these other therapies or treatment modalities may be concurrent, or the two treatments may be divided up such that the agent of the present invention may be given prior to or after the other therapy or treatment modality.

"Local administration" means direct administration by a non-systemic route at or in the vicinity of the site of an affliction, disorder, or perceived pain.

"Immunomodulator" means an agent that acts to normalize immune cell numbers or activity. The immunomodulator may restore or normalize immune cell number or activity in subjects suffering from diseases or conditions whereby the immune cell number or activity is either diminished or enhanced. The immunomodulator may be a plant, a plant extract, a plurality of plant extracts, a plant composition, a combination of plant extracts which synergize with other agents, some of which may be known immunomodulators, and other agents which may not, when used alone, exhibit immunomodulatory activity. The immunomodulator may be a chemical compound, a peptide, a polypeptide, a hormone, an antibody, an oligonucleotide or an antisense oligonucleotide. The normalization refers to conditions in which the number or activity of immune cells, including T and B lymphocytes, natural killer cells, macrophages, neutrophils and platelets are present in abnormal numbers or exert abnormal activity.

The term "antibody" as used herein includes intact molecules as well as fragments thereof, such as Fab and $F(ab')_2$, which are capable of binding the epitopic determinant. Antibodies that bind the genes or gene products of the present invention can be prepared using intact polynucleotides or polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g., a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be prepared in mice, rats, goats, sheep, swine, dogs, cats, or horses.

"AMBOVEX®" is a therapeutically effective botanical agent derived from plant matter. It is prepared from the plants described herein that belong to the family Ranunculaceae by the methods described below. It has immunomodulatory properties as demonstrated in the examples provided below. Its chemical constituents are not well defined. Furthermore, the active moiety has not been identified.

As used herein, "viral load" refers to the amount of virus present in a subject as measured by standard molecular and/or immunological diagnostic techniques. Viral load can be correlated with the likelihood of a response to antiviral therapy or to therapies with immunomodulators (Herve, M., Hepatology (2003), 37 (6)). It may refer to the number of viral particles in a sample of tissue obtained from a subject, such as that obtained by tissue biopsy, or it may refer to the amount of virus in whole blood, or in serum or plasma. The viral load may be measured by PCR or RT-PCR and may be expressed in number of viral nucleic acid copies or equivalents per milliliter. As related to the present application, a "low level" of HCV RNA may be defined as being below 1 million IU (2 million copies) per mL. Most patients with chronic hepatitis C have levels of HCV RNA (viral load) between 100,000 and 10,000,000 copies per mL. Expressed as IU, these averages are 50,000 to 5 million IU.

"Hepatic Activity Index" refers to a numerical scoring system used to assess the histological activity in patients with chronic active hepatitis. An illustration of the method used in this scoring system is shown in Table 3, with further detailed description in the following references by Ishak et al and Knodell et al. (Ishak K, et al. Histological grading and staging of chronic hepatitis. *J Hepatol* (1995), 22:696-699; Knodell R G, et al. Formulation and application of a numerical scoring system for assessing histological activity in asymptomatic chronic active hepatitis. *Hepatology* (1981), 1(5):431-5). Evaluation of the severity of the chronic hepatitis is made according to the amount of fibrosis and existence of cirrhosis in the liver on histological examination of a biopsied liver tissue. Several scoring systems have been proposed to evaluate the amount of fibrosis in chronic hepatitis. These are shown in Table 4, and as further outlined in the following references (Desmet et al., Hepatology, (1994), 19:1513; Knodell et al., Hepatology, (1981), 1:431; Scheuer et al., J Hepatology, (1991), 13:372.)

TABLE 3

Hepatic Activity Index Grading System

Modified HAI Grading: Necroinflammatory Scores

| Periportal or Periseptal Interface Hepatitis (piecemeal necrosis) (A) | Score | Confluent Necrosis (B) | Score | Focal (spotty) Lytic Necrosis, Apoptosis, and Focal Inflammation* (C) | Score | Portal Inflammation (D) | Score |
|---|---|---|---|---|---|---|---|
| Absent | 0 | Absent | 0 | Absent | 0 | None | 0 |
| Mild (focal, few portal areas) | 1 | Focal confluent necrosis | 1 | One focus or less per 10 × objective | 1 | Mild, some or all portal areas | 1 |
| Mild/moderate (focal, most portal areas) | 2 | Zone 3 necrosis in some areas | 2 | Two to four foci per 10 × objective | 2 | Moderate, some or all portal areas | 2 |
| Moderate (continuous around <50% of tracts or septa) | 3 | Zone 3 necrosis in most areas | 3 | Five to ten foci per 10 × objective | 3 | Moderate/marked, all portal areas | 3 |

TABLE 3-continued

Hepatic Activity Index Grading System

| | | | | | | | |
|---|---|---|---|---|---|---|---|
| Severe (continuous around >50% of tracts or septa) | 4 | Zone 3 necrosis + occasional portal-central (P-C) bridging | 4 | More than ten foci per 10 × objective | 4 | Marked, all portal areas | 4 |
| | | Zone 3 necrosis + multiple P-C bridging | 5 | | | | |
| | | Panacinar or multiacinar necrosis | 6 | | | | |

References
1. Ishak K, et al. Histological grading and staging of chronic hepatitis. J Hepatol 1995: 22: 696-699.
2. Knodell RG, et al. Formulation and application of a numerical scoring system for assessing histological activity in asymptomatic chronic active hepatitis. Hepatology 1981; 1(5): 431-5
Total Modified HAI = __/18
*Does not include diffuse sinusoidal infiltration by inflammatory cells.

| Additional features which should be noted but not scored: | Immunohistochemical findings |
|---|---|
| Bile-duct inflammation and damage<br>Lymphoid follicles<br>Steatosis, mild moderate or marked<br>Hepatocellular dysplasia, large- or small-cell<br>Adenomatous hyperplasia<br>Iron or copper overload<br>Intracellular inclusions (eg. PAS-positive globules, Mallory bodies) | Information on viral antigens, lymphocyte subsets or other features, when available, should be recorded and may be semi-quantitatively expressed |

Modified Staging: architectural changes, fibrosis and cirrhosis*

| Change | Score |
|---|---|
| No fibrosis | 0 |
| Fibrous expansion of some portal areas, with or without short fibrous septa | 1 |
| Fibrous expansion of most portal areas, with or without short fibrous septa | 2 |
| Fibrous expansion of most portal areas with occasional portal to portal (P—P) bridging | 3 |
| Fibrous expansion of portal areas with marked bridging [portal to portal (P—P) as well as portal to central (P-C)] | 4 |
| Marked bridging (P—P and/or P-C) with occasional nodules (incomplete cirrhosis) | 5 |
| Cirrhosis, probable or definite | 6 |

References
1. Ishak K, et al. Histological grading and staging of chronic hepatitis. J Hepatol 1995; 22: 696-699.
2. Knodell RG, et al. Formulation and application of a numerical scoring system for assessing histological activity in asymptomatic chronic active hepatitis. Hepatology 1981; 1(5): 431-5
*Additional features which should be noted but not scored: Intra-acinar fibrosis, perivenular ('chicken wire' fibrosis) and phlebosclerosis of terminal hepatic venules.

The "polymerase chain reaction (PCR)" technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment (i.e., an amplicon) whose termini are defined by the 5' ends of the primers. PCR is reported to be capable of producing a selective enrichment of a specific DNA sequence by a factor of $10^9$. The PCR method is also described in Saiki et al., 1985, Science, 230:1350. "Reverse transcription-polymerase chain reaction (RT-PCR)" is the most sensitive technique for mRNA detection and quantitation currently available. RT-PCR can also be used for cloning, cDNA library construction, probe synthesis, differential display, and signal amplification in in situ hybridizations. The technique consists of two parts: synthesis of cDNA from RNA by reverse transcription (RT) and amplification of a specific cDNA by polymerase chain reaction (PCR).

General Description

The present invention relates to the identification of pharmacologically active compositions derived from plants in the family Ranunculaceae. More particularly, extracts from this family of plants have been prepared and specific biological activity useful for treatment of hepatic disorders and immunological deficiencies has been attributed to these extracts, when used alone or in combination with other agents. In particular, the present invention provides for compositions comprising botanicals from the family: Ranunculaceae, subclass: Dicotyledonae; Crassinucelli, superorder: Ranunculales. Compositions comprising these botanicals include but are not limited to; *Actaea, Anemone, Ranunculus,* and *Nigella*, or extracts thereof, which are useful in treating liver diseases, particularly those with viral etiology. Furthermore, compositions comprising botanicals from *Actaea Rubra, Anemone hepatica, Anemone Nemorosa, Nigella sativa, Ranunculus Arvensis* are particularly effective in treating the disorders described herein, including but not limited to, hepatitic disorders including those having viral etiology and for treatment of immunological disorders. The compositions of the present invention are derived from various botanicals or medicinal plants, which have a long history of human consumption. The compositions of the invention are obtained through the procedures described herein and have demonstrated outstanding efficacy for treatment of patients with hepatic disorders. Compositions of the present invention have also exhibited immunomodulatory activities in experimental rats. The preferred compositions contain the botanical ingredients in concentrations of not less than 20% w/v. The treatment can be effective when used either as a therapeutic or when given prophylactically and may be administered orally, parenterally, topically, as suppository or via nasal mucosa. The treatment may be delivered in a single dose, multi-doses or via a slow release mechanism.

In a preferred embodiment, the plant material is treated to increase the surface area. This can be accomplished by grinding, shredding, macerating of leaves flowers, seeds, and stems. Plant material is then extracted in a polar solvent, such as those known to one skilled in the art. Non-limiting examples of polar solvents are water, alcohols, and ethers. Extraction can be accomplished using an extraction tank. The liquid extract is concentrated, optionally using vacuum. The concentrated extract is collected, and the remaining vegetative material is discarded. Preservatives such as benzyl alcohol, benzoic acid or sodium benzoate are then added to the mixture, which is then sterilized by one of the following methods, UV irradiation, filtration or by laser beam. Any other standard methods for sterilization, which are known to those skilled in the art, may be used. The mixture is then freeze dried (lyophilized). Afterwards, the dried material is then brought to not less than 20% w/v by addition of excipients.

The present invention further relates to methods of treatment of hepatic disorders or immunological deficiencies in a subject animal. Preferably the subject is a mammal, more preferably the subject is a human. The compositions of the present invention may be used therapeutically or prophylactically.

Pharmaceutical Compositions and Methods of Administration

The present invention also provides pharmaceutical compositions used in the method of the invention. Such compositions comprise a therapeutically effective amount of the extracts from at least one plant in the family Ranunculaceae, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

The therapeutic agent, whether it be a polypeptide, analog or active fragment-containing compositions or small organic molecules, are conventionally administered by various routes including intravenously, intramuscularly, subcutaneously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of binding capacity desired. Precise amounts of active ingredient required to be administered depend on the judgment of the practitioner and are peculiar to each individual. Suitable regimes for initial administration and subsequent injections are also variable, but are typified by an initial administration followed by repeated doses at intervals by a subsequent injection or other administration.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Administration of the compositions to the site of injury, the target cells, tissues, or organs, may be by way of oral administration as a pill or capsule or a liquid formulation or suspension. It may be administered via the transmucosal, sublingual, nasal, rectal or transdermal route. Parenteral administration may also be via intravenous injection, or intramuscular, intradermal or subcutaneous. Due to the nature of the diseases or conditions for which the present invention is being considered, the route of administration may also involve delivery via suppositories. This is especially true in conditions whereby the ability of the patient to swallow is compromised.

The plant compositions or extracts may be provided as a liposome formulation. Liposome delivery has been utilized as a pharmaceutical delivery system for other compounds for a variety of applications. See, for example Langer (1990) Science 249:1527-1533; Treat et al. (1989) in *Liposomes in the Therapy of Infectious Disease and Cancer*, Lopez-Berestein and Fidler (eds.), Liss: New York, pp. 353-365 (1989). Many suitable liposome formulations are known to the skilled artisan, and may be employed for the purposes of the present invention. For example, see: U.S. Pat. No. 5,190,762.

In a further aspect, liposomes can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier; and the like.

Transdermal delivery of the plant compositions or extracts is also contemplated. Various and numerous methods are known in the art for transdermal administration of a drug, e.g., via a transdermal patch. It can be readily appreciated that a transdermal route of administration may be enhanced by use of a dermal penetration enhancer.

Controlled release oral formulations may be desirable. The plant composition or extract may be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Pulmonary delivery may be used for treatment as well. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Ophthalmic and nasal delivery may be used in the method of the invention. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextrins. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

The compositions and extracts of the present invention are also suited for transmucosal delivery. In particular, the compositions and extracts are particularly suited for sublingual, buccal or rectal delivery of agents that are sensitive to degradation by proteases present in gastric or other bodily fluids having enhanced enzymatic activity. Moreover, transmucosal delivery systems can be used for agents that have low oral bioavailability. The compositions of the instant invention comprise the plant extract dissolved or dispersed in a carrier that comprises a solvent, an optional hydrogel, and an agent that enhances transport across the mucosal membrane. The solvent may be a non-toxic alcohol known in the art as being useful in such formulations of the present invention and may include, but not be limited to ethanol, isopropanol, stearyl alcohol, propylene glycol, polyethylene glycol, and other solvents having similar dissolution characteristics. Other such solvents known in the art can be found in "The Handbook of Pharmaceutical Excipients", published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980).

Any transmucosal preparation suitable for administering the components of the present invention or a pharmaceutically acceptable salt thereof can be used. Particularly, the mixture is any preparation usable in oral, nasal, or rectal cavities that can be formulated using conventional techniques well known in the art. Preferred preparations are those usable in oral, nasal or rectal cavities. For example, the preparation can be a buccal tablet, a sublingual tablet, and the like preparation that dissolve or disintegrate, delivering drug into the mouth of the patient. A spray or drops can be used to deliver the drug to the nasal cavity. A suppository can be used to deliver the mixture to the rectal mucosa. The preparation may or may not deliver the drug in a sustained release fashion.

A specific embodiment for delivery of the components of the present invention is a mucoadhesive preparation. A mucoadhesive preparation is a preparation which upon contact with intact mucous membrane adheres to said mucous membrane for a sufficient time period to induce the desired therapeutic or nutritional effect. The preparation can be a semisolid composition as described for example, in WO 96/09829. It can be a tablet, a powder, a gel or film comprising a mucoadhesive matrix as described for example, in WO 96/30013. The mixture can be prepared as a syrup that adheres to the mucous membrane.

Suitable mucoadhesives include those well known in the art such as polyacrylic acids, preferably having the molecular weight between from about 450,000 to about 4,000,000, for example, Carbopol™934P; sodium carboxymethylcellulose (NaCMC), hydroxypropylmethylcellulose (HPMC), or for example, Methocel™ K100, and hydroxypropylcellulose.

The delivery of the components of the present invention can also be accomplished using a bandage, patch, device and any similar device that contains the components of the present invention and adheres to a mucosal surface. Suitable transmucosal patches are described for example in WO 93/23011, and in U.S. Pat. No. 5,122,127, both of which are hereby incorporated by reference. The patch is designed to deliver the mixture in proportion to the size of the drug/mucosa interface. Accordingly, delivery rates can be adjusted by altering the size of the contact area. The patch that may be best suited for delivery of the components of the present invention may comprise a backing, such backing acting as a barrier for loss of the components of the present invention from the patch. The backing can be any of the conventional materials used in such patches including, but not limited to, polyethylene, ethyl-vinyl acetate copolymer, polyurethane and the like. In a patch that is made of a matrix that is not itself a mucoadhesive, the matrix containing the components of the present invention can be coupled with a mucoadhesive component (such as a mucoadhesive described above) so that the patch may be retained on the mucosal surface. Such patches can be prepared by methods well known to those skilled in the art.

Preparations usable according to the invention can contain other ingredients, such as fillers, lubricants, disintegrants, solubilizing vehicles, flavors, dyes and the like. It may be desirable in some instances to incorporate a mucous membrane penetration enhancer into the preparation. Suitable penetration enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate), and related compounds.

The administration of the compositions and extracts of the present invention can be alone, or in combination with other compounds effective at treating the various medical conditions contemplated by the present invention. Also, the compositions and formulations of the present invention, may be administered with a variety of analgesics, anesthetics, or anxiolytics to increase patient comfort during treatment.

The compositions of the invention described herein may be in the form of a liquid. The liquid may be delivered as a spray, a paste, a gel, or a liquid drop. The desired consistency is achieved by adding in one or more hydrogels, substances that absorb water to create materials with various viscosities. Hydrogels that are suitable for use are well known in the art. See, for example, Handbook of Pharmaceutical Excipients, published by The American Pharmaceutical Association and The Pharmaceutical Society of Great Britain (1986) and the Handbook of Water-Soluble Gums and Resins, ed. By R. L. Davidson, McGraw-Hill Book Co., New York, N.Y. (1980).

Suitable hydrogels for use in the compositions include, but are not limited to, hydroxypropyl cellulose, hydroxypropyl methyl cellulose, sodium carboxymethyl cellulose and polyacrylic acid. Preferred hydrogels are cellulose ethers such as hydroxyalkylcellulose. The concentration of the hydroxycellulose used in the composition is dependent upon the particular viscosity grade used and the viscosity desired in the final product. Numerous other hydrogels are known in the art and the skilled artisan could easily ascertain the most appropriate hydrogel suitable for use in the instant invention.

The mucosal transport enhancing agents useful with the present invention facilitate the transport of the agents in the claimed invention across the mucosal membrane and into the blood stream of the patient. The mucosal transport enhancing agents are also known in the art, as noted in U.S. Pat. No. 5,284,657, incorporated herein by reference. These agents may be selected from the group of essential or volatile oils, or from non-toxic, pharmaceutically acceptable inorganic and organic acids. The essential or volatile oils may include peppermint oil, spearmint oil, menthol, eucalyptus oil, cinnamon oil, ginger oil, fennel oil, dill oil, and the like. The suitable inorganic or organic acids useful for the instant invention include but are not limited to hydrochloric acid, phosphoric acid, aromatic and aliphatic monocarboxylic or dicarboxylic acids such as acetic acid, citric acid, lactic acid, oleic acid, linoleic acid, palmitic acid, benzoic acid, salicylic acid, and other acids having similar characteristics. The term "aromatic" acid means any acid having a 6-membered ring system characteristic of benzene, whereas the term "aliphatic" acid refers to any acid having a straight chain or branched chain saturated or unsaturated hydrocarbon backbone.

Other suitable transport enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate), and related compounds.

When the compositions and extracts of the instant invention are to be administered to the oral mucosa, the preferred pH should be in the range of pH 3 to about pH 7, with any necessary adjustments made using pharmaceutically acceptable, non-toxic buffer systems generally known in the art.

For topical delivery, a solution of the plant extract in water, buffered aqueous solution or other pharmaceutically-acceptable carrier, or in a hydrogel lotion or cream, comprising an emulsion of an aqueous and hydrophobic phase, at a concentration of between 50 µM and 5 mM, is used. A preferred concentration is about 1 mM. To this may be added ascorbic acid or its salts, or other ingredients, or a combination of these, to make a cosmetically-acceptable formulation. Metals should be kept to a minimum. It may be preferably formulated by encapsulation into a liposome for oral, parenteral, or, preferably, topical administration.

The invention provides methods of treatment comprising administering to a subject a therapeutically effective amount of at least one plant extract. In one embodiment, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

The amount of plant extract which is optimal in treating hepatic disorders or treating immune deficiencies can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Treatment Group

A subject in whom administration of plant compositions or extracts is an effective therapeutic regiment is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Furthermore, the administration of plant compositions or extracts may be given at the time of or after the identification of a hepatic disorder or immune deficiency, alone, or in combination with other agents known to be beneficial for ameliorating the symptoms or decreasing viral load or enhancing the number or activity of immune cells in patients having hepatitis or an immune deficiency.

In one embodiment, the subject suitable for treatment by the method of the invention is a subject determined to be suffering from hepatitis or other hepatic disorders. This determination may be made clinically by methods known to one of skill in the art. Generally, the determination of a subject suffering from hepatic disorders is by liver functions tests. For example, serum levels of SGPT (Serum Glutamic-Pyruvic Transaminase)—also called ALT (Alanine Aminotransferase), and SGOT (Serum Glutamic-Oxaloacetic Transaminase)—also called AST (Aspartate Aminotransferase) are often used to assess liver function. These are liver enzymes that leak out into the bloodstream in conditions in which hepatocytes are damaged or die. The blood levels of these two enzymes increase in cases of hepatitis. Further, prothrombin and albumin may be measured. These are two proteins that are synthesized by the liver and secreted into the blood. Low serum albumin and prothrombin concentration indicate poor liver function. They are usually normal in chronic liver disease until cirrhosis and significant liver damage is present. Platelet counts can also be affected in chronic liver diseases. These are the smallest of the blood cells. In some individuals with liver diseases, the spleen becomes enlarged as blood flow (microcirculation) through the liver is impeded.

This can lead to platelets being sequestered in the enlarged spleen. In chronic liver diseases, the platelets count usually falls only after cirrhosis has developed. A liver biopsy can also be performed to assess the degree of hepatic damage. This test provides the most accurate information on the stage of fibrosis and grade of necroinflammation, and the Hepatic Activity Index (HAI), both of which have prognostic significance.

In another embodiment, the subject suitable for treatment by the method of the invention is a subject determined to be harboring hepatitis virus, in particular, hepatitis C. Patients with anti-HCV antibodies, HCV RNA, elevated serum aminotransferase levels, and evidence of chronic hepatitis on liver biopsy are subjects who are suitable for treatment with the compositions of the present invention. This diagnostic determination may be made by methods known to one of skill in the art. Generally, the presence of hepatitis C (HCV) may be confirmed using techniques such as enzyme immunoassay (EIA). Alternatively, immunoblot assays such as a "Western blot" can be used to confirm anti-HCV reactivity. In this assay, serum is incubated on nitrocellulose strips on which four recombinant viral proteins are blotted. Color changes indicate that antibodies are adhering to the proteins. An immunoblot is considered positive if two or more proteins react and is considered indeterminate if only one positive band is detected. In some clinical situations, confirmatory testing by immunoblotting is helpful, such as for the person with anti-HCV detected by EIA who tests negative for HCV RNA. The EIA anti-HCV reactivity could represent a false-positive reaction, recovery from hepatitis C, or continued virus infection with levels of virus too low to be detected (the last occurs only rarely when sensitive PCR or TMA assays are used). If the immunoblot test for anti-HCV is positive, the patient has most likely recovered from hepatitis C and has persistent antibody. If the immunoblot test is negative, the EIA result was probably a false positive. Immunoblot tests are routine in blood banks when an anti-HCV-positive sample is found by EIA. Immunoblot assays are highly specific and valuable in verifying anti-HCV reactivity. Indeterminate tests require further follow-up testing, including attempts to confirm the specificity by repeat testing for HCV RNA.

Further confirmatory tests may include use of the polymerase chain reaction (PCR), or reverse transcriptase polymerase chain reaction (RT-PCR) or transcription mediated amplification (TMA). The presence of HCV RNA in serum indicates an active infection. Testing for HCV RNA may be helpful in patients in whom EIA testing for anti-HCV are unreliable. For example, immunocompromised patients may test negative for anti-HCV despite having HCV infection, since they may not be able to mount an antibody response for detection with EIA. Similarly, patients with acute hepatitis may test negative for anti-HCV upon initial testing. Antibody is present in almost all patients by one month after the initial onset of the illness. Therefore, it is recommended that patients with acute hepatitis who upon initial testing are negative should be retested at a later date. Furthermore, patients who have had an organ transplant and are taking immunosuppressive drugs may also initially test negative for HCV using EIA, since they may not be able to mount an antibody response to HCV. However, in these situations, HCV RNA testing is the most reliable method for demonstrating that hepatitis C infection is present and usually results in a confirmatory diagnosis. A PCR assay has now been approved by the Food and Drug Administration for general use. This assay will detect HCV RNA in serum down to a lower limit of 50 to 100 copies per milliliter (mL) which is equivalent to 25 to 50 international units (IU). Almost all patients with chronic hepatitis will test positive by these assays.

In another embodiment, the invention provides for decreasing the viral load in liver-cancer patients by administration of the compositions of the present invention to a patient in need of such therapy. In patients with hepatitis virus, several methods are available for measuring the concentration or level of virus in serum, which is an indirect assessment of viral load. These methods include a quantitative PCR and a branched DNA (bDNA) test. Unfortunately, these assays are not well standardized, and different methods from different laboratories can provide different results on the same specimen. In addition, serum levels of HCV RNA can vary spontaneously by 3- to 10-fold over time. Nevertheless, when performed carefully, quantitative assays provide important insights into the nature of hepatitis C. Most patients with chronic hepatitis C have levels of HCV RNA (viral load) between 100,000 and 10,000,000 copies per mL. Expressed as IU, these averages are 50,000 to 5 million IU.

Viral levels as measured by HCV RNA do not correlate with the severity of the hepatitis or with a poor prognosis (as in HIV infection); but viral load does correlate with the likelihood of a response to antiviral therapy or to therapies with immunomodulators. Rates of response to a course of alpha interferon and ribavirin are higher in patients with low levels of HCV RNA. There are several definitions of a "low level" of HCV RNA, but the usual definition is below 1 million IU (2 million copies) per mL.

There are 6 known genotypes and more than 50 subtypes of hepatitis C. The genotype of infection is helpful in defining the epidemiology of hepatitis C. More important, knowing the genotype or serotype (genotype-specific antibodies) of HCV is helpful in making recommendations and counseling regarding therapy. Patients with genotypes 2 and 3 are two to three times more likely to respond to interferon-based therapy than patients with genotype 1. Furthermore, when using combination therapy, the recommended dose and duration of treatment depends on the genotype. For patients with genotypes 2 and 3, a 24-week course of combination treatment using interferon and 800 milligrams (mg) of ribavirin daily is adequate, whereas for patients with genotype 1, a 48-week course and full dose of ribavirin (1,000 to 1,200 mg daily) is recommended. For these reasons, testing for HCV genotype is often clinically helpful. Once the genotype is identified, it need not be tested again; genotypes do not change during the course of infection.

The following biochemical changes are indicative of infection with hepatitis C virus:

In chronic hepatitis C, increases in the alanine and aspartate aminotransferases range from 0 to 20 times (but usually less than 5 times) the upper limit of normal.

Alanine aminotransferase (ALT) levels are usually higher than aspartate aminotransferase (AST) levels, but that finding may be reversed in patients who have cirrhosis.

Alkaline phosphatase and gamma glutamyl transpeptidase are usually normal. If elevated, they may indicate cirrhosis.

Rheumatoid factor and low platelet and white blood cell counts are frequent in patients with severe fibrosis or cirrhosis, providing clues to the presence of advanced disease.

The enzymes lactate dehydrogenase and creatine kinase are usually normal.

Albumin levels and prothrombin time are normal until late-stage disease.

Iron and ferritin levels may be slightly elevated.

Liver biopsy is not necessary for diagnosis but is helpful for grading the severity of disease and staging the degree of fibrosis and permanent architectural damage. Hematoxylin and eosin stains and Masson's trichrome stain are used to grade the amount of necrosis and inflammation and to stage the degree of fibrosis. Specific immunohistochemical stains for HCV have not been developed for routine use. Liver biopsy is also helpful in ruling out other causes of liver disease, such as alcoholic liver injury or iron overload.

HCV causes the following changes in liver tissue:

Necrosis and inflammation around the portal areas, so-called "piecemeal necrosis" or "interface hepatitis."

Necrosis of hepatocytes and focal inflammation in the liver parenchyma.

Inflammatory cells in the portal areas ("portal inflammation").

Fibrosis, with early stages being confined to the portal tracts, intermediate stages being expansion of the portal tracts and bridging between portal areas or to the central area, and late stages being frank cirrhosis characterized by architectural disruption of the liver with fibrosis and regeneration. Several scales are used to stage fibrosis, most commonly a scale from 0 to 4 where 0 indicates none and 4 indicates cirrhosis. Stage 1 and 2 fibrosis is limited to the portal and periportal areas. Stage 3 fibrosis is characterized by bridges of fibrosis bands linking up portal and central areas.

Grading and staging of hepatitis by assigning scores for severity are helpful in managing patients with chronic hepatitis. The degree of inflammation and necrosis can be assessed as none, minimal, mild, moderate, or severe. The degree of fibrosis can be similarly assessed. Scoring systems are particularly helpful in clinical studies on chronic hepatitis. Several scoring systems have been proposed to evaluate the amount of fibrosis in chronic hepatitis. These are shown in Table 4, and as outlined in the following references (Desmet et al., Hepatology, (1994), 19:1513; Knodell et al., Hepatology, (1981), 1:431; Scheuer et al., J Hepatology, (1991), 13:372.)

TABLE 4

Scoring Systems for Liver Fibrosis and Cirrhosis

| Score | Description | Knodell | Sciot and Desmet (unpublished) | Scheuer |
|---|---|---|---|---|
| 0 | No fibrosis | No fibrosis | None | None |
| 1 | Mild fibrosis | Fibrous portal expansion | Periportal fibrous expansion | Enlarged, fibrotic portal tracts |
| 2 | Moderate fibrosis | (blank) | Porto-portal septa (>1 septum) | Periportal or portal-portal septa, but intact architecture |
| 3 | Severe fibrosis | Bridging fibrosis (portal—portal or portal-central linkage) | Portocentral septa (>1 septum) | Fibrosis with architectural distortion, but no obvious cirrhosis |
| 4 | Cirrhosis | Cirrhosis | Cirrhosis | Probable or definite cirrhosis |

Liver biopsy is an invasive procedure that is expensive and not without complications. At least 20 percent of patients have pain requiring medications after liver biopsy. More uncommon complications include puncture of another organ, infection, and bleeding. Significant bleeding after liver biopsy occurs in $1/100$ to $1/1,000$ cases, and deaths are reported in $1/5,000$ to $1/10,000$ cases. Obviously, noninvasive means of grading and staging liver disease would be very helpful.

ALT levels, particularly if tested over an extended period, are reasonably accurate reflections of disease activity. Thus, patients with repeatedly normal ALT levels usually have mild necroinflammatory activity on liver biopsy. Furthermore, patients who maintain ALT levels above 5 times the upper limit of normal usually have marked necroinflammatory activity. But for the majority of patients with mild-to-moderate ALT elevations, the actual level is not very predictive of liver biopsy findings.

More important is a means to stage liver disease short of liver biopsy. Unfortunately, serum tests are not reliable in predicting fibrosis, particularly earlier stages (0, 1, and 2). When patients develop bridging (stage 3) fibrosis and cirrhosis (stage 4), serum tests may be helpful. The "danger signals" that suggest the presence of advanced fibrosis include an aspartate aminotransferase (AST) that is higher than ALT (reversal of the ALT/AST ratio), a high gamma glutamyl transpeptidase or alkaline phosphatase, a low platelet count (which is perhaps the earliest change), rheumatoid factor, elevations in globulins, and, of course, abnormal bilirubin, albumin or prothrombin time. Physical findings of a firm liver, or enlarged spleen or prominent spider angionata or palmar erythema, are also danger signals. While none of these findings are perfect, their presence should raise the suspicion of significant fibrosis and lead to evaluation for treatment earlier rather than later.

In another embodiment of the invention, a subject suitable for treatment by the method of the invention is a subject who is immunocompromised by virtue of a viral disease such as HIV infection, or alternatively, may be immunocompromised by virtue of treatment with various chemotherapeutic drugs or radiation therapy, as is standard therapy for cancer patients.

The determination as to whether one is immunocompromised is made by way of immunological assays or by determination of blood cell counts. Determination of specific blood cell populations can be assessed using standard assays known to those skilled in the art. Standard staining techniques for cytological evaluation such as hematoxylin and eosin or Giemsa stains can be used to stain peripheral blood cells and differential cell counts can be done by those skilled in the art. In this manner, one can determine the number and type of white blood cells present in a blood sample, including lymphocytes, neutrophils, monocytes, eosinophils, basophils, as well as red blood cells. Based on known standards, one can determine whether a blood cell count falls within a normal range (*Laboratory Diagnosis*, Bennington, Fouty and Hougie, The Macmillan Co., Collier-Macmillan Limited, London, pp. 482-503), or whether there are deficiencies in certain cell populations, such as lymphocytes or neutrophils, this being indicative of an immunocompromised state, thus predisposing these patients to viral or bacterial infections. Alternatively, labeled antibodies (e.g. fluorescently labeled) are readily available which recognize and bind to cells bearing markers specific for certain immune cell types. One example of this is the T helper cells, which bear CD4 receptors and are known as CD4+ cells. Other T cells include the cytolytic T cells, which have CD8 receptors and are thus called CD8+ cells. Antibodies are available which are specific for these cell types, and when conjugated to a protein such as fluoresceine or rhodamine can be used to detect the presence and/or numbers (percentage) of these cell types in a patient blood sample. The presence or absence of these cell populations can be determined by standard microscopic techniques or by fluorescence activated cell sorting (FACS) analysis. Other standard functional assays can be used to determine whether a patient is immunocompromised. In one assay, a peripheral blood sample is collected from a patient, the cells are separated from the liquid portion of the blood, and are plated under sterile conditions on to tissue culture plates. The cells are then incubated with mitogens specific for particular cell types, for example, concanavalin A for T lymphocytes. If T cells are present, they will multiply in the presence of the mitogen and the amount of cellular proliferation can be measured using tritiated thymidine incorporation as an indicator. In the absence of the particular cell type, the level of thymidine incorporation will be diminished. As will be appreciated by those skilled in the art, there are other methods available for determining the level of immunocompetency in an individual, and the methods cited herein are not to be taken as limitations of what is encompassed by the methods of the invention.

In another embodiment, patients having both HCV and HIV may be candidates suitable for treatment by the method of the present invention provided that there are no contraindications. Hepatitis C tends to be more rapidly progressive in patients with HIV co-infection, and end-stage liver disease has become an increasingly common cause of death in HIV-positive individuals. For these reasons, therapy for hepatitis C with the compositions of the present invention are envisioned, either as a stand-alone therapy, or as adjunct therapy with interferon or other immunomodulators or with an anti-viral such as ribavirin, should be recommended even in HIV-infected patients with early and mild disease. Once HIV infection becomes advanced, complications of therapy are more difficult and response rates are less. The decision to treat people co-infected with HIV must take into consideration the concurrent medications and medical conditions. In many of these indefinite situations, the indications for therapy should be reassessed at regular intervals.

Screening for Immune Enhancing Agents

The invention features a screening method for identifying active botanical extracts capable of enhancing the immune system, comprising (a) exposing (treating) lymphocytes with and without treatment with test extracts; and (b) determining the effect of the test extract on lymphocyte populations, wherein test compounds capable of increasing immune cell integrity or preserving immune cell numbers are identified as immune enhancing agents. A preferred embodiment includes an in vitro screening method for the identification of novel compositions and/or plant extracts useful for treating hepatic disorders or treating immune deficiencies, comprising, incubation of blood cells obtained from a mammal with either a vehicle control, or with at least one of the extracts from the plants of the present invention as a positive control, or with a test extract, and monitoring the effect of the extracts on blood cell number and/or proliferation, or activity/function or on expression of cell surface markers. A further embodiment includes a screening method for identifying extracts capable of protecting immune cells from damage, comprising (a) treating immune cells with cytotoxic compounds in vitro or in vivo with and without treatment with a test extract; and (b) determining the effect of the test extract on the immune cell population, wherein a test extract capable of increasing cell survival is identified as an immunoprotective agent. A yet further embodiment provides for an in vivo method of screening for novel compositions and/or plant extracts useful for treating hepatic disorders or treating immune deficiencies comprising, injecting mammals with LPS, dividing the mammals into various treatment groups, treating one group with a vehicle control, the second group is treated with at least one extract from the plants of the present invention as a positive control, and a test extract, and obtaining blood cells from the mammals and monitoring the blood cells for cell surface markers or proliferative capacity or immune cell function and/or activity.

EXAMPLES

Example 1

In a preferred embodiment of the invention, the composition of the invention comprises at least one of the botanical plants *Actaea rubra*, *Anemone hepatica*, *Anemone nemorosa*, *Nigella sativa*, and *Ranunculus arvensis*, or extracts thereof.

Although the administration of a composition containing only *Anemone hepatica* and/or *Nigella sativa* will be effective in treating hepatic and immunological disorders, the synergism between all the botanicals render the administration of a combination of each botanical plant very desirable.

The procedures provided herein result in an extract such that the concentration of the extract's medicinal contents yield a sterile preparation that contains not less than 20% weight per volume. In a preferred embodiment, the plant material is treated to increase the surface area. This can be accomplished by grinding, shredding, macerating of leaves flowers, seeds, and stems. Plant material is then extracted in a polar solvent, such as those known to one skilled in the art. Non-limiting examples of polar solvents are water, alcohols, and ethers. Extraction can be accomplished using an extraction tank. The liquid extract is concentrated, optionally using vacuum. The concentrated extract is collected, and the remaining vegetative material is discarded. Preservatives such as benzyl alcohol, benzoic acid or sodium benzoate are then added to the mixture, which is then sterilized by one of the following methods, UV irradiation, filtration or by laser beam. Any other standard methods for sterilization, which are known to those skilled in the art, may be used. The mixture is then freeze dried (lyophilized). Afterwards, the dried material is then brought to not less than 20% w/v by addition of excipients.

Example 2

A sterile preparation for intra-muscular injection of the composition prepared according to Example 1, was evaluated in a clinical study involving fifty one (51) patients infected with chronic hepatitis C virus (CHCV), with clinical stages 0/6 to 3/6, with Hepatic Activity Index (H.A.I.) ranging from 1/18 to 9/18, using a randomized placebo controlled protocol. Thirty six (36) patients were randomly selected as the case-group, and fifteen (15) as the placebo-group. The treatment involved a 1-ml intra-muscular injection three times a week, for two periods; period one: twenty four weeks (24) weeks, end period two: forty eight weeks, with evaluations at time zero (to establish a base line), and then at every eight weeks until the end of the study. The following parameters were studied:

Quantitative-PCR (Quantitative-Polymerase Chain Reaction) This test is used to assess the level of virus in serum. It involves the amplification of the nucleic acid associated with virus several million times, by using the "chain reaction", in order to bring it up to a measurable levels. As the amplification process is fully controlled, the quantity of virus present in the sample (the viral load) can be calculated with a great degree of accuracy. Viral load is evaluated every 24 weeks.

SGPT (Serum Glutamic-Pyruvic Transaminase)—also called ALT (Alanine Aminotransferase), and SGOT (Serum Glutamic-Oxaloacetic Transaminase)—also called AST (Aspartate Aminotransferase) These are liver enzymes that leak out into the bloodstream in conditions in which hepatocytes are damaged or die. The blood levels of these two enzymes increase in cases of hepatitis. These enzymes are evaluated every eight weeks.

Prothrombin and Albumin These are two proteins that are synthesized by the liver and secreted into the blood. Low serum albumin and prothrombin concentration indicate poor liver function. They are usually normal in chronic liver disease until cirrhosis and significant liver damage is present. These are evaluated every eight weeks.

Platelet count These are the smallest of the blood cells. In some individuals with liver diseases, the spleen becomes enlarged as blood flow (microcirculation) through the liver is impeded. This can lead to platelets being sequestered in the enlarged spleen. In chronic liver diseases, the platelets count usually falls only after cirrhosis has developed. This is evaluated every eight weeks.

Total Leukocyte count (White Blood Cell count) Leukocytes are white blood cells whose main function is to fight infection. They defend the body against invasion by foreign organisms, in part, by phagocytosis. They are part of the immune system. White blood cell (WBC) counts are evaluated every eight weeks.

Hemoglobin (HGB) is composed of globin protein and heme, which contains iron atoms and the red pigment porphyrin. HGB is important determinant of anemia. This is evaluated every eight weeks.

Liver biopsy This test provides the most accurate information on the stage of fibrosis and grade of necroinflammation, and the Hepatic Activity Index (HAI), both of which have prognostic significance. This is evaluated at 48 months.

Results 66.6% of the cases responded, with a significant 70% decrease in the quantity of the serum HCV (viral load) of the case group ($p<0.001$) (FIG. 1).

Figure 2:
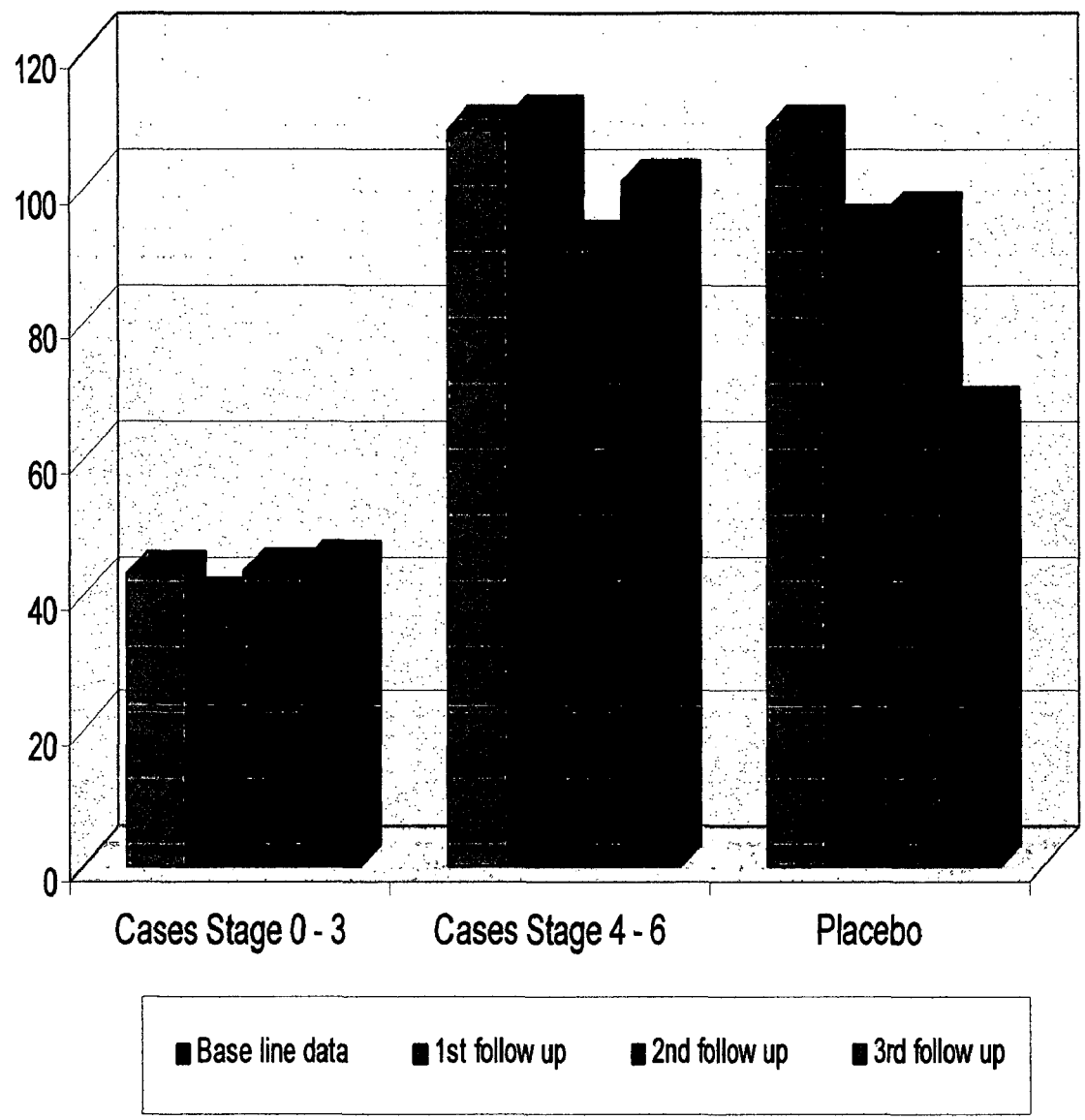
FIG. 2. ALT (ALT=SGPT) of the two case groups with pathological stages of 0/6-3/6 and 4/6-6/6 and the placebo group.

There was also a significant decrease in liver enzyme ALT of the case-group ($p<0.0001$) (FIG. 2).

On the other hand, there was a significant increase in the ALT of the placebo-group ($p<0.03$).

Figure 3:
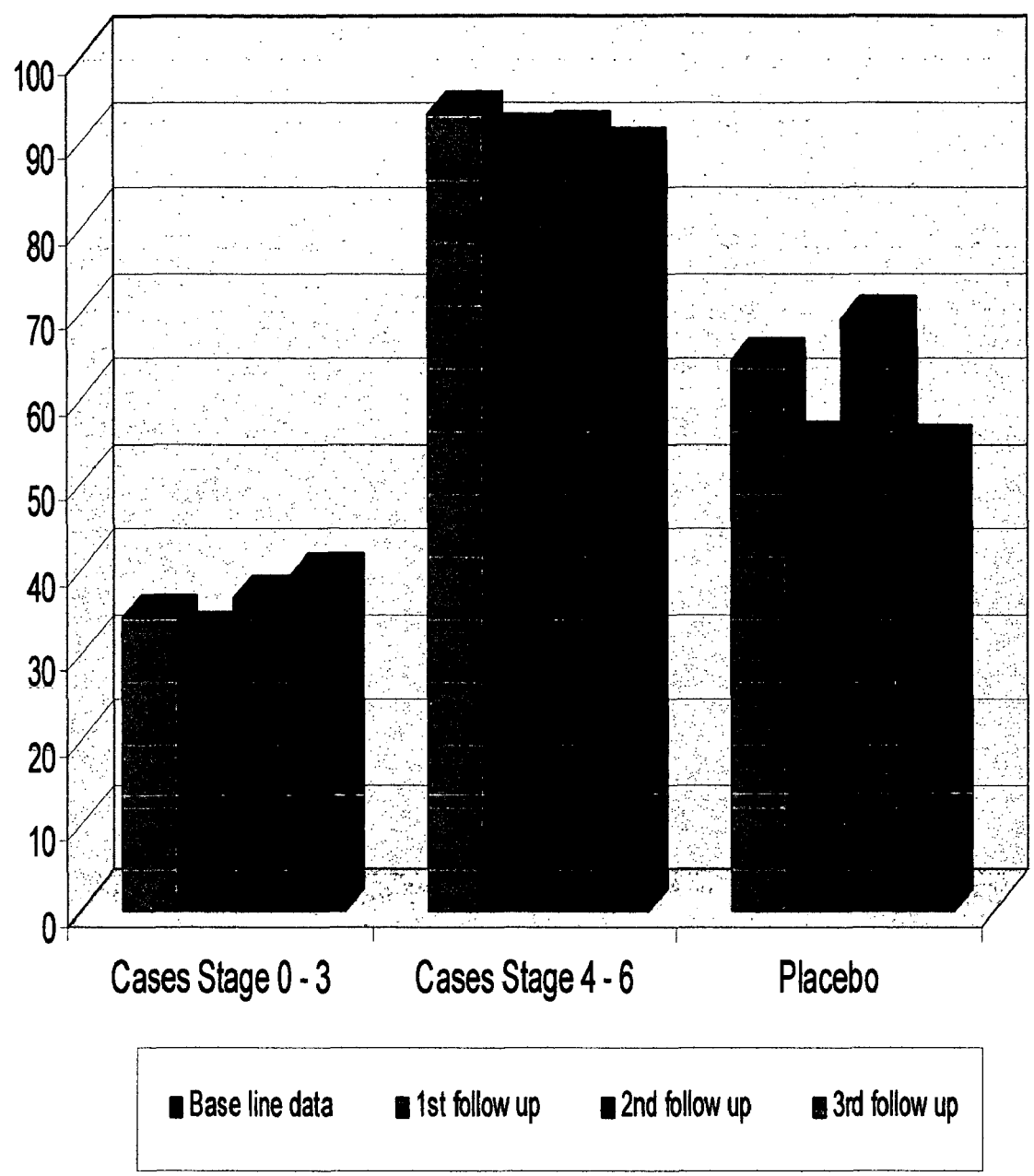
FIG. 3. AST (AST=SGOT) of the two case groups with pathological stages of 0/6-3/6 and 4/6-6/6 and the placebo group.

Furthermore, there was a significant decrease in liver enzyme AST of the case-group ($p<0.0001$) (FIG. 3). Meanwhile, there was a significant increase in the AST of the placebo-group ($p<0.04$).

Figure 4:
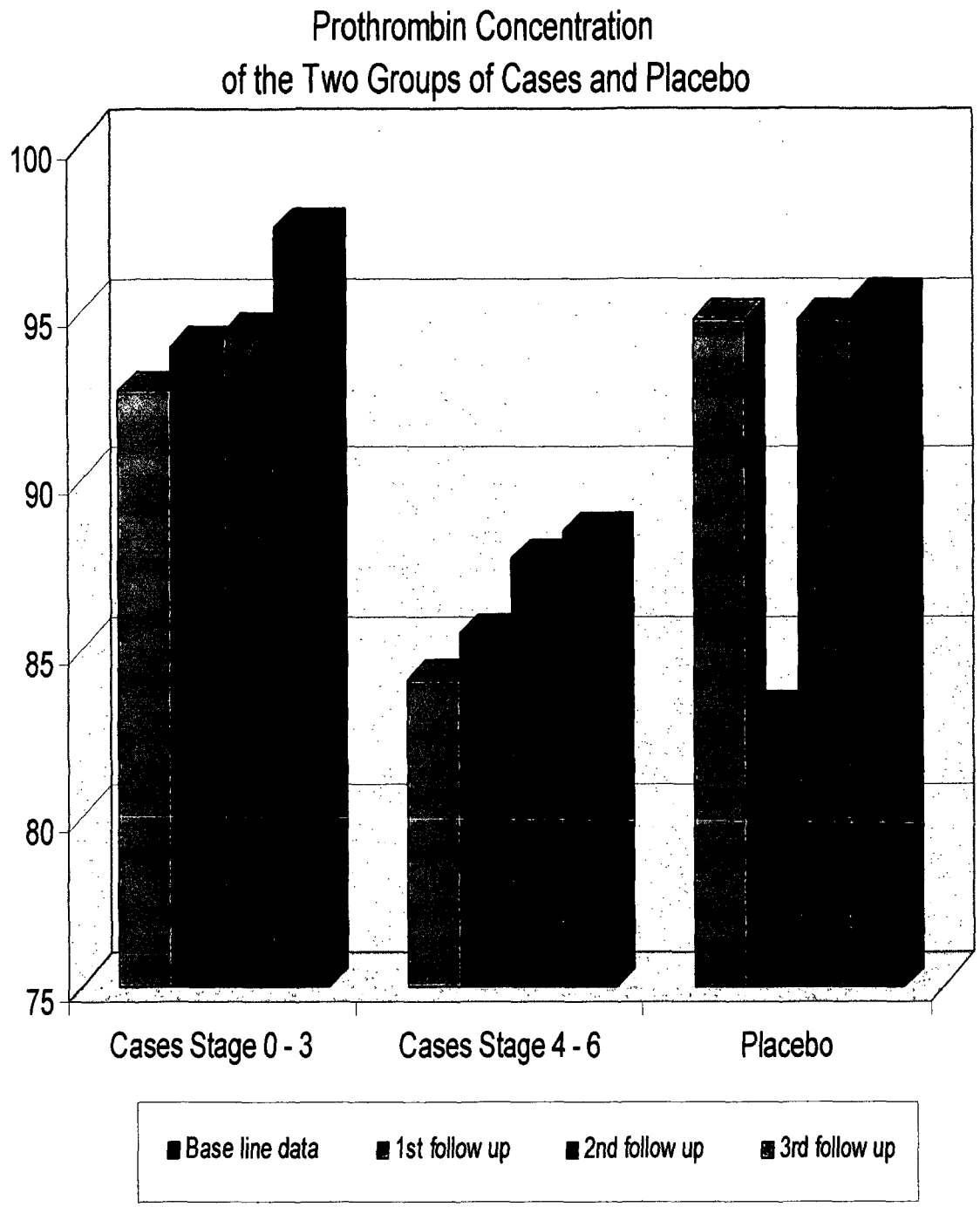
FIG. 4. Prothrombin concentration of the two case groups with pathological stages of 0/6-3/6 and 4/6-6/6 and the placebo group.
Figure 5:
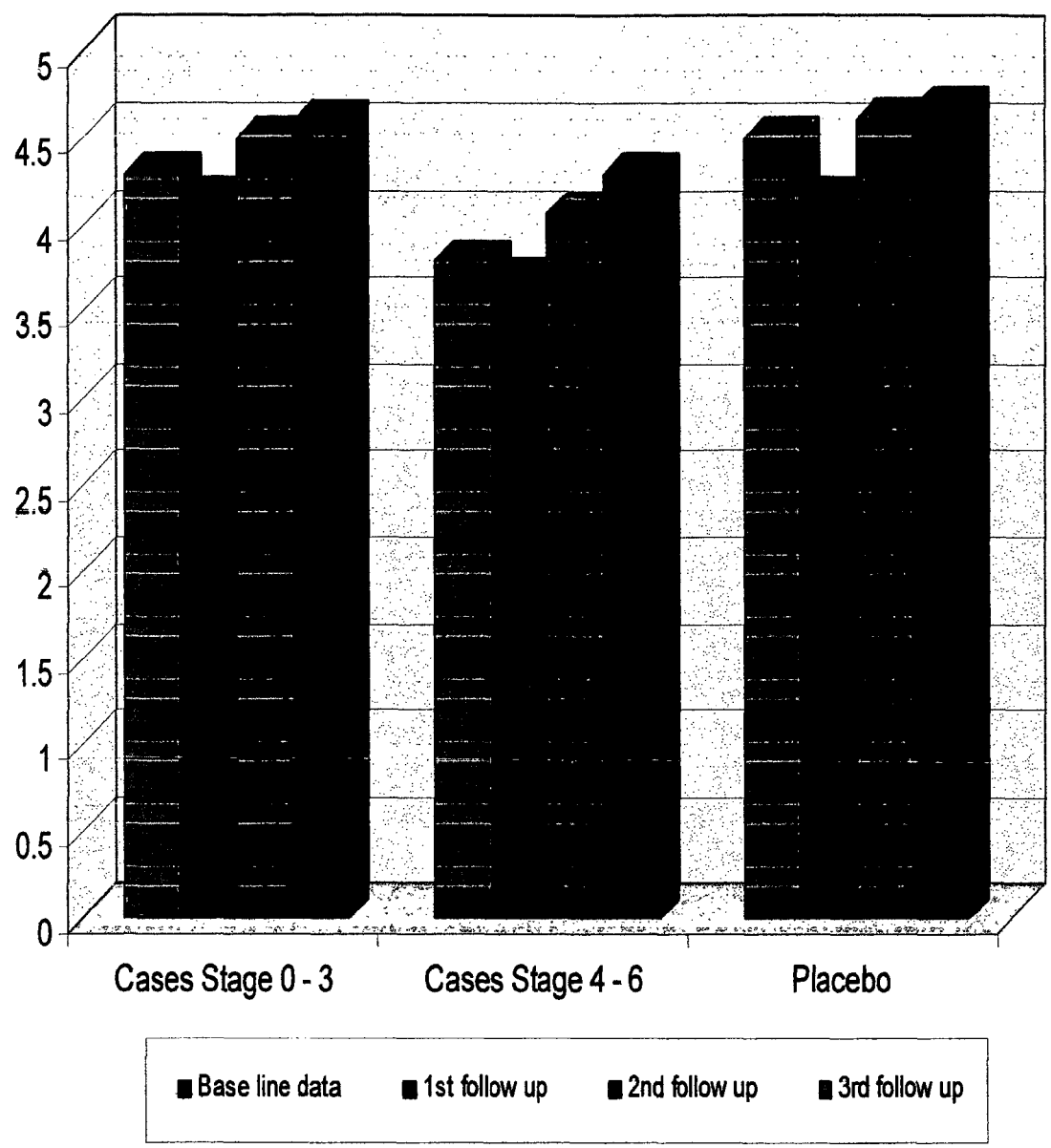
FIG. 5. Albumin of the two case groups with pathological stages of 0/6-3/6 and 4/6-6/6 and the placebo group.

No changes were observed for serum Albumin of both the case-group and the placebo group (FIG. 5), meanwhile, Prothrombin of both the case-group and the placebo-group were significantly decreased, ($p<0.03$) and ($p<0.01$) respectively (FIG. 4).

Figure 6:
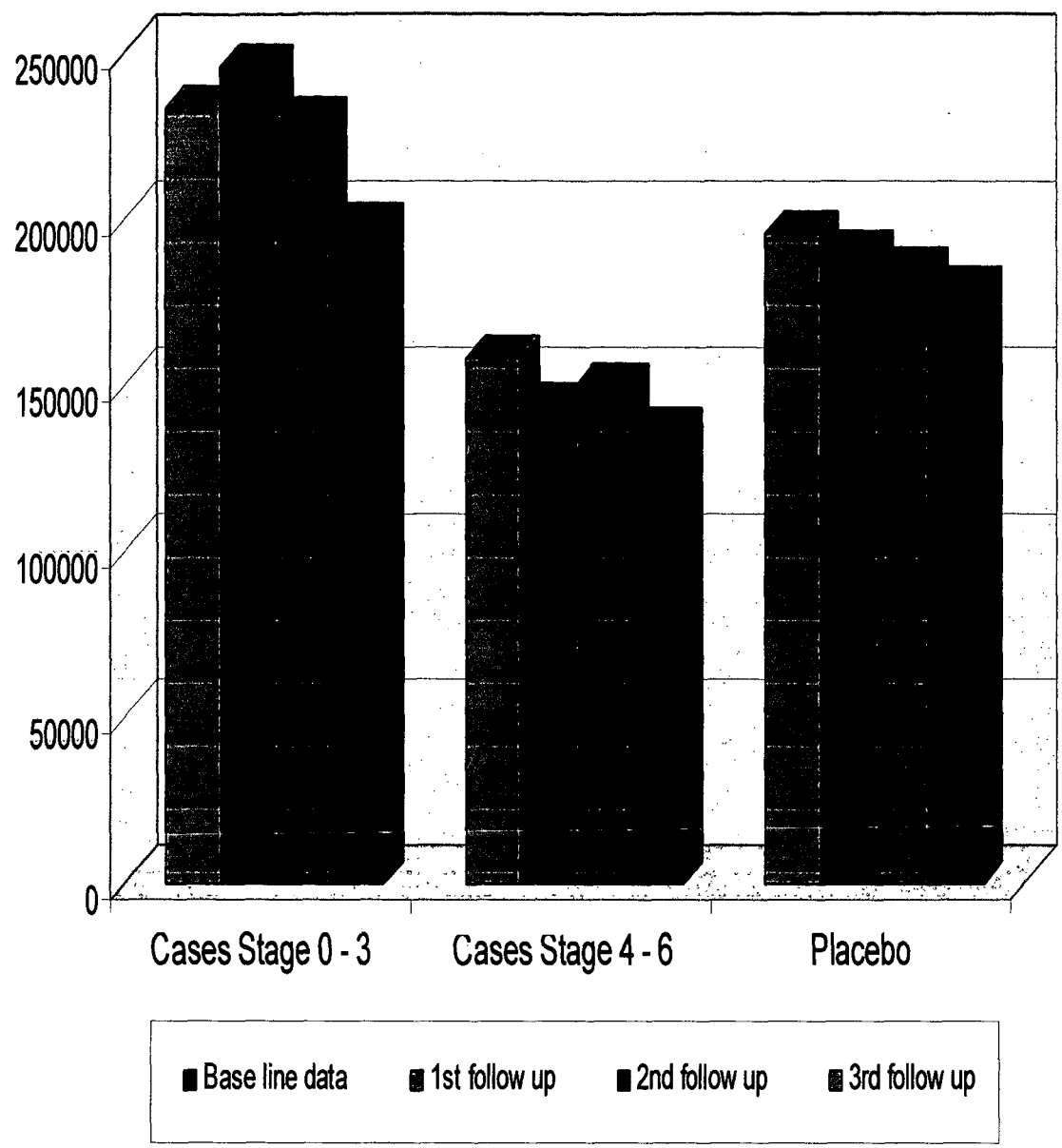
FIG. 6. Platelet counts of the two case groups with pathological stages of 0/6-3/6 and 4/6-6/6 and the placebo group.

Significant 18% increase in the Platelet count of the case-group ($p<0.0001$), compared to a significant 9% increase in the Platelet counts of the placebo-group ($p<0.0001$) (FIG. 6).

Figure 7:
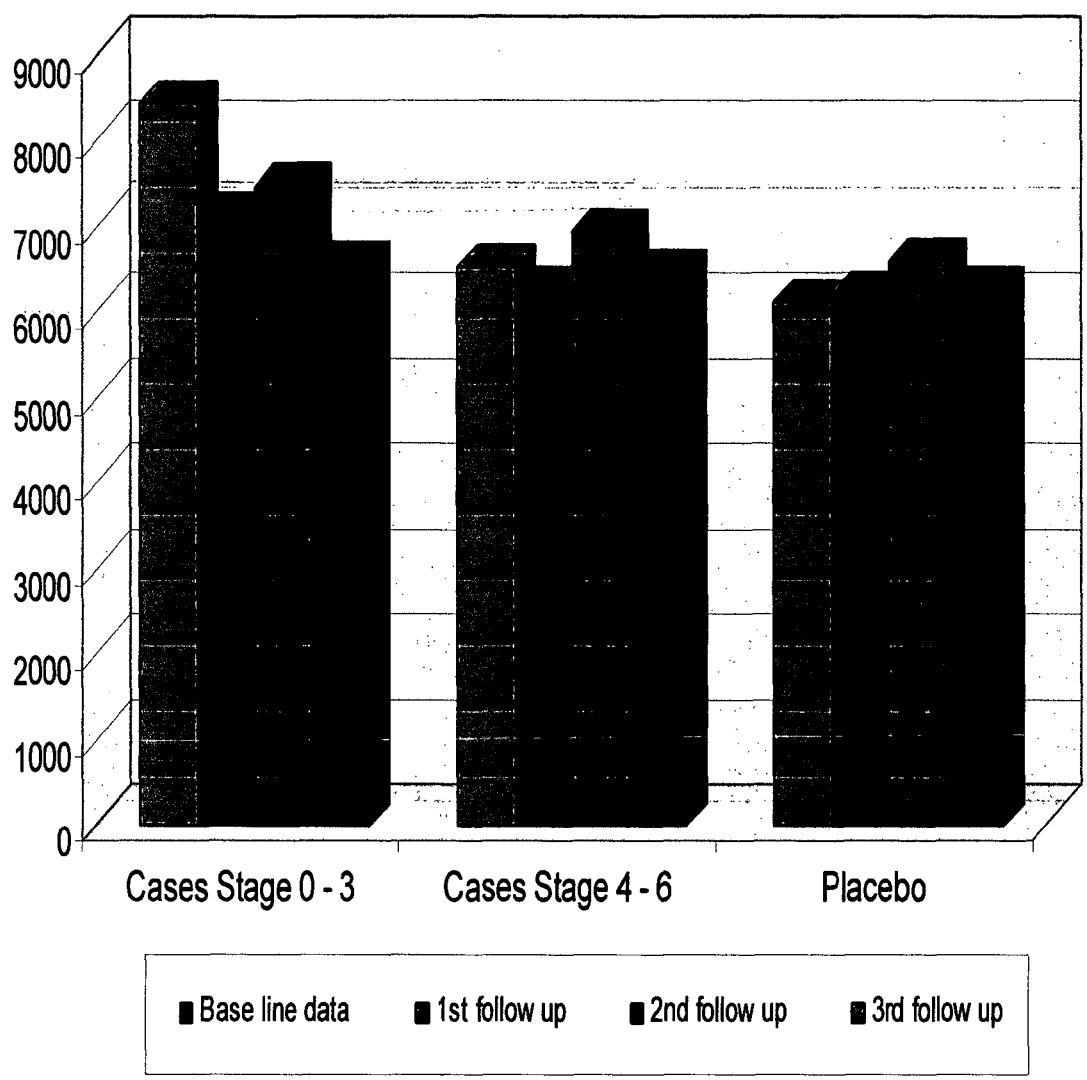
FIG. 7. Total leukocyte counts of the two case groups with pathological stages of 0/6-3/6 and 4/6-6/6 and the placebo group.

Significant 28% increase for the Total Leukocyte count of the case group, ($p<0.01$), compared to no change for the placebo-group (FIG. 7).

Figure 8:
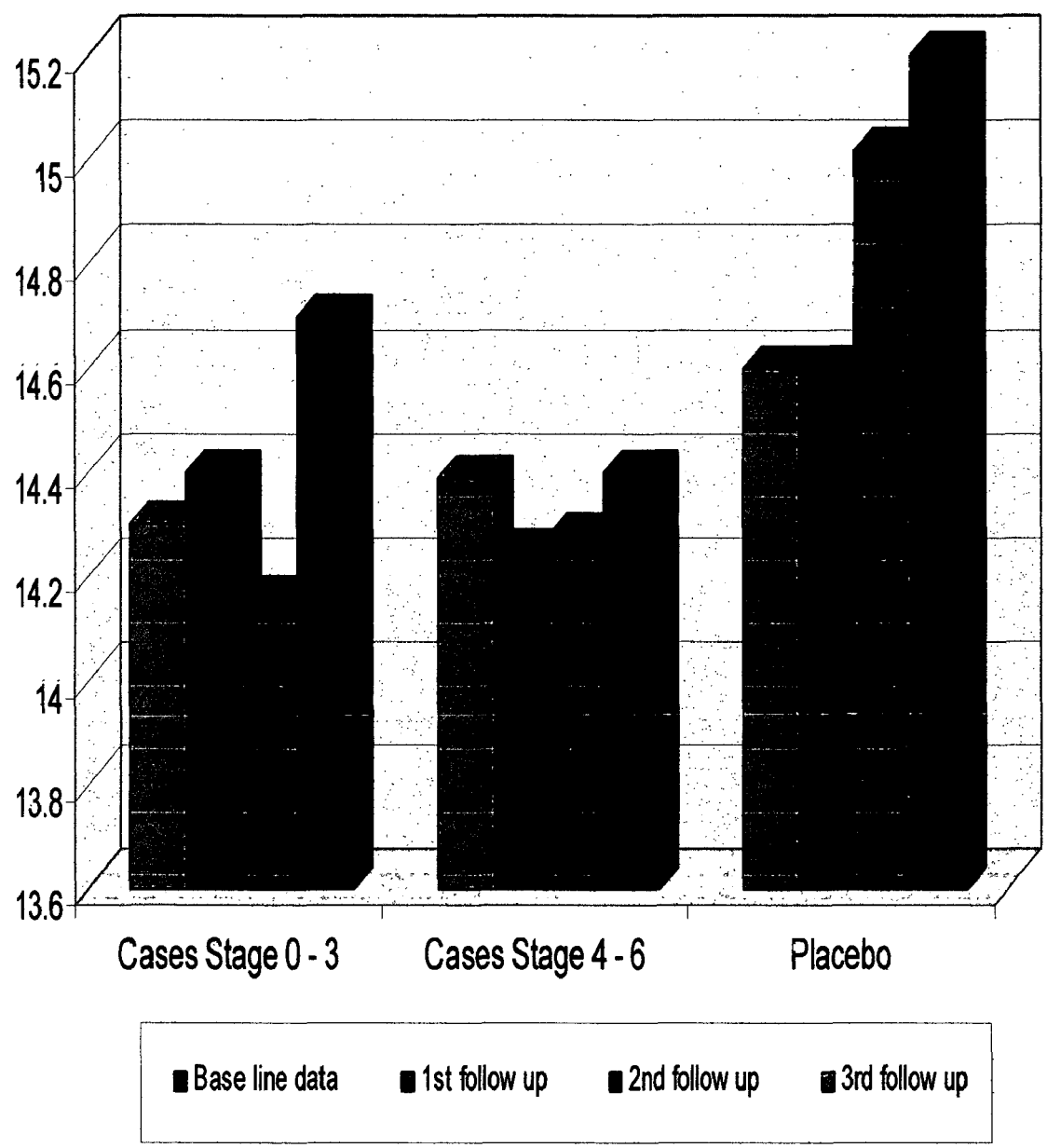
FIG. 8. Hemoglobin quantitation of the two case groups with pathological stages of 0/6-3/6 and 4/6-6/6 and the placebo group.

Significant decrease in Hemoglobin (HB) blood content of both the case-group, ($p<0.0001$), and the placebo-group ($p<0.0002$), but both stayed within the normal range. This shows that the compositions have no adverse effect on the HB blood content (FIG. 8).

The results of the study demonstrate that the composition was capable of modifying disease activity in CHCV.

Example 3

A sterile preparation for intra-muscular injection of the composition prepared according to Example 1, was evaluated in a clinical study involving thirty eight (38) patients infected with chronic hepatitis C virus (CHCV), with advanced clinical stages 4/6 to 6/6, i.e. liver cirrhosis, end-stage liver disease, and liver cancer, with a corresponding Hepatic Activity Index (H.A.I.), ranging from 7/18 to 13/18, using a randomized placebo controlled protocol. Twenty three (23) patients were randomly selected as the case-group and fifteen (15) as the placebo-group. The treatment involved a 1 ml intramuscular injection three times a week for two periods: period one: twenty four (24) weeks, and period two: forty eight (48) weeks, with evaluations at time zero (to establish a base line), and then at every eight weeks until the end of the study. The same parameters as in EXAMLPE 2 were studied, i.e. PCR, ALT, AST, Prothrombin and Albumin, Platelets, total Leukocytes, Hemoglobin, and liver biopsy.

Results:

73% of the cases responded, with a significant 66.6% decrease in the quantity of the serum HCV (viral load) of the case group ($p<0.05$). It should be noted that two (2) patients; Patient #16, and Patient #18 were identified with liver cancer. In spite of their terminal clinical stage, the compositions were able to lower their viral load (PCR) by 67% and 99.4% respectively.

Significant increase in liver enzyme ALT for both the case-group ($p<0.0009$), and the placebo-group ($p<0.03$).

No change in liver enzyme AST of the case-group. Meanwhile, a significant increase in the AST of the placebo-group ($p<0.04$). This could be due to the hepatocytes heavy damage because of the cirrhosis, end stage liver disease, and/or liver cancer.

No changes were observed for serum Albumin. The Prothrombin of the case-group showed no change, meanwhile the placebo-group had significantly decreased, ($p<0.01$).

Significant 16% increase in the Platelet count of the case-group ($p<0.0001$), compared to a significant 9% increase in the Platelet counts of the placebo-group ($p<0.0001$).

Significant increase for the Total Leukocyte count of the case group, (p<0.0001), compared to no change for the placebo group.

No adverse effect of the compositions on the hemoglobin (HB) blood content of the case-group, meanwhile there was a significant decrease in the (BB) blood content of the placebo-group, (p<0.0002).

Similarly, the results of the study demonstrate that the composition was capable of modifying disease activity in CHCV patients with the clinically advanced stages, i.e. 4/6, 5/6, and 6/6.

A person skilled in the art will understand that the therapeutic effects of the composition result from a plurality of active agents in each botanical plant which when combined, act synergistically to enhance efficacy. It will also be understood that composition comprising all or a selection of such active agents, preferably in pure form, are also contemplated herein, as are liquid formulations of the composition and formulations which are suitable for slow release administration. Thus it will be understood that the composition of the invention can be administered orally, intravenously, subcutaneously, topically, as suppository or by other known means.

The compositions are effective in treating hepatic disorders generally, irrespective of their etiology since the compositions act at least in part to improve the liver function and microcirculation. The compositions may also exert their effect prophylatically, by preventing or minimizing the adverse effects of viral infections or the action of other agents, which cause liver dysfunction. Therefore, the treatment of hepatic disorders caused by viral infection, autoimmune reactions, and drug intake are contemplated herein.

The invention may be embodied in various other forms, which are understood by those skilled in the art.

Example 4

A sterile preparation for intra-muscular injection of the composition prepared according to Example 1 was evaluated in an animal study involving thirty seven (37) rats which were injected with lipopolysaccharide (LPS). These studies were focused on the safety and immunomodulatory effect of the present invention.

The primary goals of this study were to:
(1) Identify an initial safe dose, and subsequent dose escalation schemes to achieve toxicity.
(2) Identify potential target organs for toxicity to reveal any functional effects on the major physiological systems.
(3) Study the effect of this formulation on the immune system, in particular, on particular lymphocyte populations including CD4, CD8, and Natural Killer (NK) cells.

Experimental Protocol

Before the beginning of the study, 10 high temperature rat cages (PC 10198HT) and 10 wire bar lids (WBL 1019RMB), 16 oz Glass bottles (B1010) were ordered from Allentown Caging Equipment Company, Allentown, N.J. 08501.

Thirty seven (37) F334/Ntac female rats (Taconic, Germantown, N.Y. 12526) were divided into four (4) groups.

All the rats used in the study were given a number. The left ear of each rat was punched using a puncher (cat #: 337B, Fisher Scientific company). Then an ear tag (cat#: 337A, Fisher Scientific company) was inserted to the ear.

The four (4) groups are:
Group (A): Control, (No treatment)
Group (B): Infected with LPS (Lipopolysaccharide)
Group (C): LPS—infected, and treated with 1 ml per day AMBOVEX® intra-peritoneal
Group (D): Treated with escalating doses of AMBOVEX® of 1 ml intra-peritoneal, three (3) times per day for three months 60 g. of rat food (Autoclaved Taconic #31 Diet food) and drinking water was given to each cage everyday.

Rat cages were cleaned twice a week as follows; One inch of bedding (cedar chips) was spread onto an empty, clean cage, the rats were transferred from the old cage to the new clean cage, then, the old cage was cleaned with soapy water and dried. The same procedure was repeated with the next cage, and so on.

Body weight of the rats were taken two times a week (Wednesday and Friday)

Working-LPS was prepared first by adding 1 ml of sterile distilled water to 1 mg of LPS (Lipopolysaccharide—from *Salmonella typhimurium*, SIGMA—L6143), and mixed thoroughly.

The first day of the study 100 µl of working-LPS were given intraperitoneally to each rat in group (B), and group (C).

Blood samples were taken from all groups at 1 hour, 3 hours, 6 hours, 12 hours, and 24 hours, twice a week for three (3) weeks.

Before taking the blood, the tail vein was dilated by immersing the tail in 50° C. water, and blood was immediately drawn using the (25G×⅝ inch) insulin needle (BD Medsaver syringe, 1 cc, Aldrich, Milwaukee, Wis. 53209). Every day 500 µl of blood was drawn from each rat.

When taking blood from the tail vain it was punched only once, as several punches to the vain will cause it to collapse. Blood cannot be withdrawn from a collapsed vein. In this case the heart puncture could be the alternative source. For this a needle should be inserted between the $5^{th}$ rib and the left ventricle.

The blood was divided into two parts; one part was collected into lavender top microtainer tubes containing EDTA (Antech Diagnostics, Memphis, Tenn.). This blood was sent to Anthech Diagnostic Laboratories for Complete Blood Count (CBC).

Another 250 µl of blood was collected into Eppendorf tubes and centrifuge at 3000 rpm for 30 minutes. The separated serum was stored at −70° C. It was sent to Rutgers University, Piscataway, N.J. for ELISA analysis.

The following tests were performed:
a) Immune-cell count:
   CD4 (Helper Cells)
   CD8 (Suppressor T-cells)
   NK (Natural Killer Cell population)
b) Complete blood count (CBC):
   Platelets
   WBC
   Lymphocytes
   Monocytes
   Eosinophils
   Polymorphonuclear Leucocytes
   RBC
   Hemoglobin
   Hematocrit At the end of the study, two (2) rats from each group, were sacrificed using 100 l of PentoBarbital (batch #19467-005, Henry Schein Inc. Denver, Pa. 17517) to take internal organs. The spleen and the thymus were taken for CD4 and CD8 counts. Spleen and thymus was crushed in PBS+FBS solution. Then cells were separated using Fycol.

The spleen, thymus, heart, liver, kidneys, lungs, and bones (femur, tibia) were put in 10% Formaldehyde solution (Cat #23316156, Fisher scientific), and were sent to Westchester Medical Center, for histological analysis. These samples were stored at room temperature.

The carcass of the rat was stored in −70° C. until the end of the study, to be disposed by Environmental control c. Inc, Garden City Park, N.Y. 11040.

Data Analysis

Data was collected from the master Table and transferred to Microsoft Excel version 8, and then imported into the statistical software JMP version 4, SAS. Analysis was performed at ∞=0.05 (5%) level of significance.

Results

Figure 9:
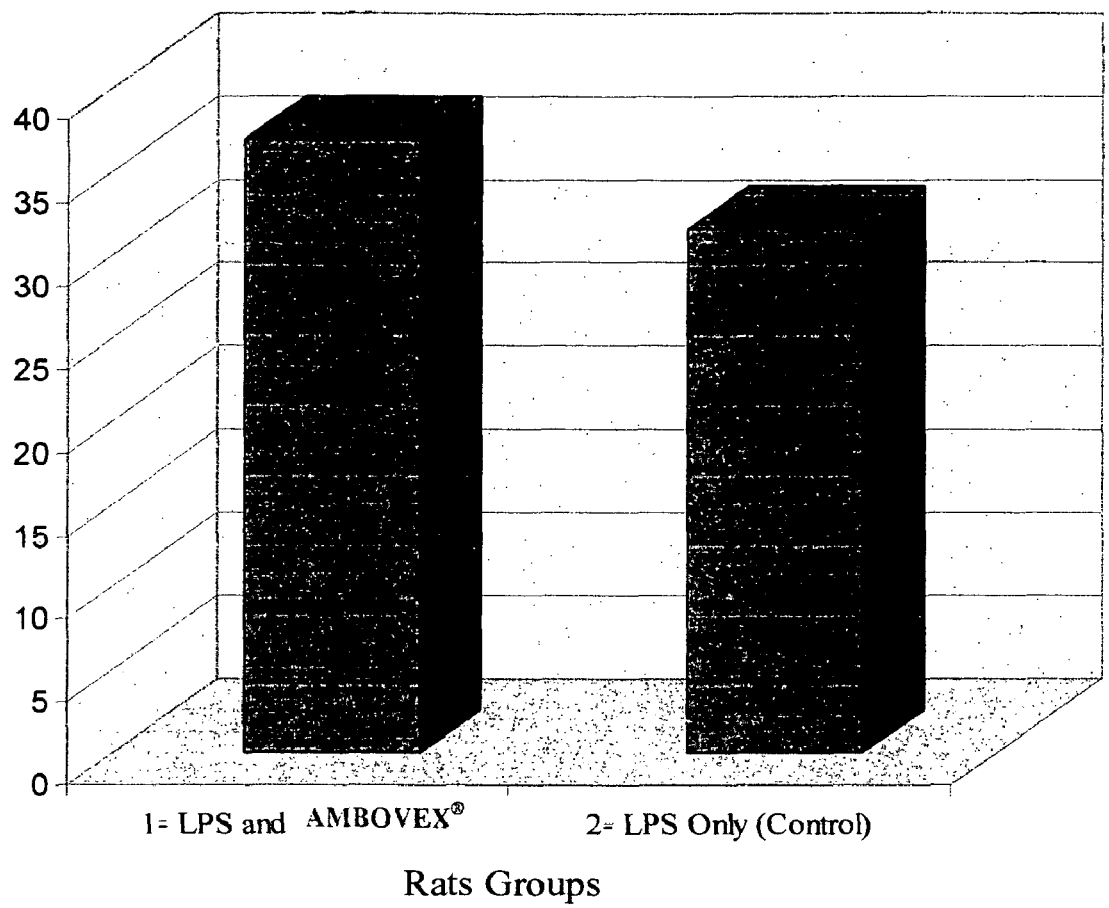
FIG. 9. Measurement of $CD4^+$ cell numbers in rats following treatment with AMBOVEX®.
Figure 10:
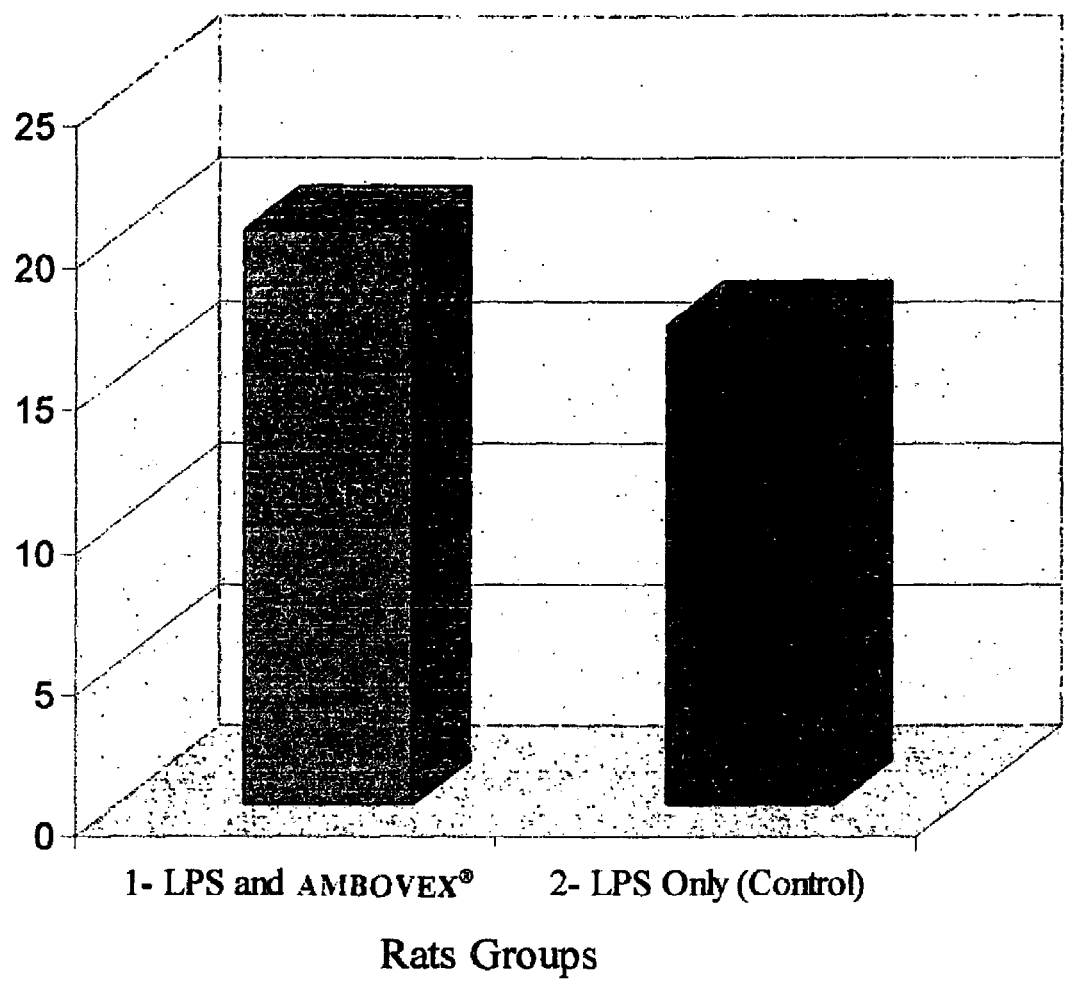
FIG. 10. Measurement of $CD8^+$ cell numbers in rats following treatment with AMBOVEX®.
Figure 11:
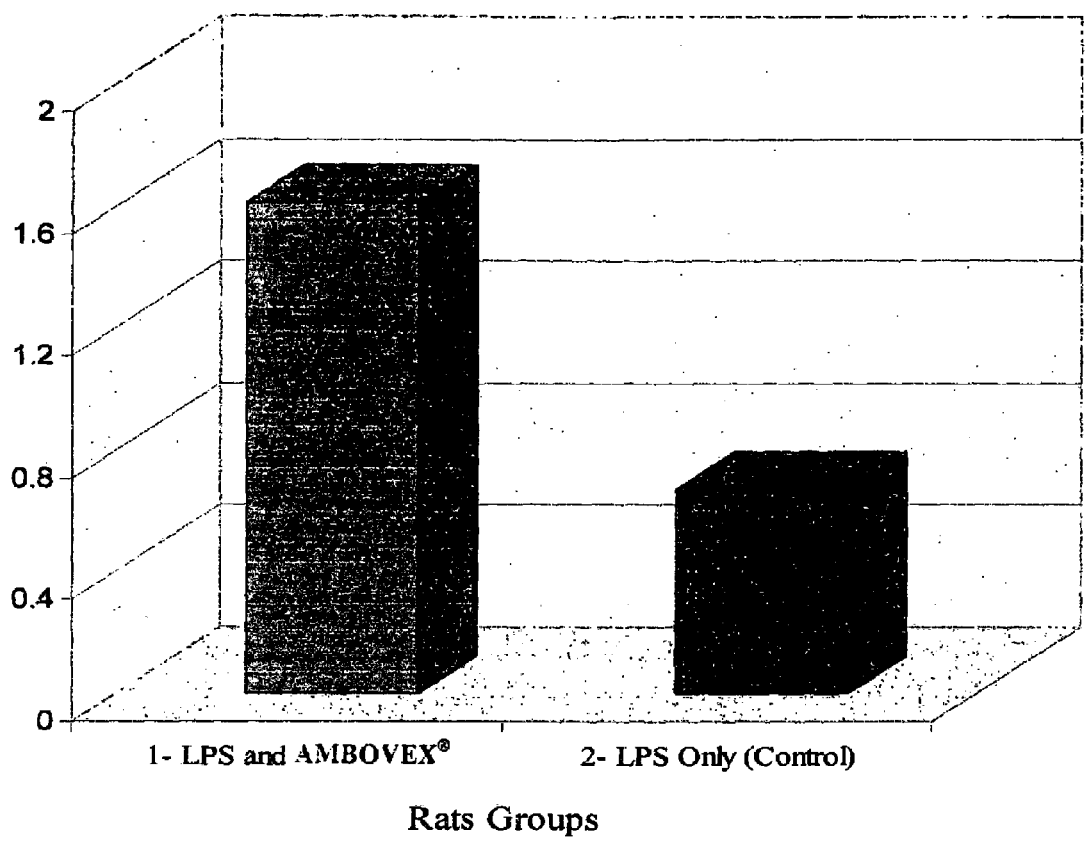
FIG. 11. Measurement of Natural Killer (NK) cells in rats treated with AMBOVEX®.

The results revealed a statistically significant increase (17%) in the CD4 (helper cells) $p<0.03$ (FIG. 9), a 20% increase in the CD8 (Suppressor T-cells) $P<0.05$ (FIG. 10), and 140% increase in the NK (Natural Killer cell populations) $p<0.01$ (FIG. 11).

The results also showed no toxic and/or pathological lesions due to the use of high doses of AMBOVEX®. "AMBOVEX®" is a therapeutically effective botanical agent derived from plant matter. It is prepared from the plants described in the present application that belong to the family Ranunculaceae by the methods described herein. It has immunomodulatory properties as demonstrated in the examples provided. Its chemical constituents are not well defined. Furthermore, the active moiety has not been identified.

The results also showed marked proliferation of the T-cells, and the B-cells, of the spleen, bone marrow, and thymus of the test group compared to the control group.

Histopathology:

Some rats from each of the test, and the control groups, were given high doses of the compositions, up to 1 ml three times a day for three months. These rats were sacrificed, and their kidneys, liver, heart, lungs, spleen, bone marrow, thymus, and brain were examined for any histopathological changes.

Materials and Methods for Histopathology of the Bone Marrow and Spleen

Sections from bone marrow and spleen were fixed in 10% buffered formative solutions for approximately five (5) days. Bone marrow sections were treated by decalcification solutions for 5 hours. Tissues from spleen and bone marrow (after data was entered into tissue processor for multiple washing in alcohol and xylene for 8 hours), tissues were then embedded in paraffin making blocks. Tissue section 5 micron section were stained by Hematoxylin and Eosin and prepared for microscopic examinations.

Conclusion

Histologic examination of the spleen showed marked increase in the T-zone lymphoid population as compared to splenic sections prior to injection. Similar findings were observed in bone marrow sections which also revealed significant increase in lymphoid populations in the post injection specimens.

The results showed no toxic and/or pathological lesions due to the use of high doses of the compositions.

Also, the results showed marked proliferation of the T-cells, and the B-cells of the spleen, bone marrow, and thymus of the test group compared to the control group. The proliferation is a major change in the immune system, which may represent a possible explanation of the mechanism of action of the compositions for inhibiting the hepatitis C virus.

FINAL RESULTS

The results showed that the compositions are safe and effective immunomodulators.

What is claimed is:

1. A pharmaceutical composition for treating a hepatic disorder and/or for increasing the number of immune cells and platelets in a patient consisting essentially of a therapeutically effective amount of a buffered aqueous extract of *Actaea rubra*, *Anemone hepatica*, *Anemone nemorosa*, *Nigella sativa*, and *Ranunculus arvensis*, and a pharmaceutically acceptable carrier, wherein the extract is present in a concentration of not less than 20% weight per volume.

2. A composition according to claim 1, wherein the composition is in a form of a tablet or capsule.

3. A composition according to claim 1, wherein the composition is in a form of a liquid or suspension.

4. A composition according to claim 1, wherein the composition is in a form of a sterile preparation for intra-muscular, subcutaneous, or intra-venous injection.

5. A composition according to claim 1, wherein the composition is in a form of nasal spray.

6. A composition according to claim 1, wherein the composition is in a form of a topical application.

7. A composition according to claim 1, wherein the composition is in a form of a transdermal system.

8. A composition according to claim 1, wherein the composition is in a form of suppository.

9. The pharmaceutical composition of claim 1, wherein the composition is effective for treating patients suffering from a hepatic disorder selected from the group consisting of chronic hepatitis, advanced/late stage hepatitis, hepatitis caused by hepatitis virus genotypes I, II, III or IV, a hepatic disorder characterized by fibrosis and/or cirrhosis, a hepatic disorder resulting from an autoimmune disease and a hepatic disorder resulting from a drug treatment.

10. The composition of claim 9, wherein the patients suffering from said hepatic disorder exhibit advanced stage liver disease characterized by fibrosis and cirrhosis, and wherein treating with said composition results in modifying disease activity, including but not limited to, a decrease in hepatitis viral load, and a decrease in liver enzymes alanine aminotransferase (ALT) levels and aspartate aminotransferase (AST) levels.

11. The composition of claim 1, wherein said composition is effective in treating the cirrhosis and fibrosis associated with an advanced/late stage hepatic disorder.

* * * * *